US008002799B2

(12) United States Patent
Chin et al.

(10) Patent No.: US 8,002,799 B2
(45) Date of Patent: Aug. 23, 2011

(54) SYSTEM AND METHOD FOR SPINE FIXATION

(75) Inventors: Kingsley R. Chin, Philadelphia, PA (US); Christopher A. Chang, Beverly, MA (US)

(73) Assignee: Spinefrontier LLS, Philadelphia, PA (US)

( * ) Notice: Subject to any disclaimer, the term of this patent is extended or adjusted under 35 U.S.C. 154(b) by 1069 days.

(21) Appl. No.: 11/779,526

(22) Filed: Jul. 18, 2007

(65) Prior Publication Data

US 2008/0021480 A1 Jan. 24, 2008

Related U.S. Application Data

(60) Provisional application No. 60/832,468, filed on Jul. 21, 2006.

(51) Int. Cl.
*A61B 17/70* (2006.01)
*A61B 17/88* (2006.01)
(52) U.S. Cl. .............................. 606/246; 606/80; 606/96
(58) Field of Classification Search .................. 606/246, 606/279, 301, 305, 308, 319, 80, 86 R, 90, 606/96, 99, 104, 105, 86 A, 191; 604/104
See application file for complete search history.

(56) References Cited

U.S. PATENT DOCUMENTS

| 2,406,952 | A | * | 9/1946 | Josepho ........................ 81/452 |
| 2,697,433 | A | * | 12/1954 | Zehnder ........................ 606/96 |
| 3,547,114 | A | * | 12/1970 | Haboush ........................ 606/71 |
| 6,221,082 | B1 | | 4/2001 | Marion et al. |
| 6,485,518 | B1 | | 11/2002 | Cornwall et al. |
| 6,540,747 | B1 | | 4/2003 | Marino |
| 6,562,046 | B2 | | 5/2003 | Sasso |
| 2005/0216026 | A1 | | 9/2005 | Culbert |
| 2006/0030872 | A1 | | 2/2006 | Culbert et al. |
| 2006/0085010 | A1 | | 4/2006 | Lieberman |
| 2006/0184177 | A1 | | 8/2006 | Echeverri |

* cited by examiner

*Primary Examiner* — Eduardo C Robert
*Assistant Examiner* — David Comstock
(74) *Attorney, Agent, or Firm* — AKC Patents LLC; Aliki K. Collins

(57) ABSTRACT

A system for attaching first and second fixation elements at a predetermined angle relative to each other to first and second locations of a vertebra, respectively includes a first guide wire configured to be inserted into the first location of the vertebra, an angular guide system comprising first and second guide arms configured to be set at the predetermined angle relative to each other and the first guide arm is configured to be inserted over the first guide wire and a second guide wire configured to be inserted through the second guide arm into the second location of the vertebra. The second guide wire includes first and second members configured to pivot relative to each other.

10 Claims, 26 Drawing Sheets

SYSTEM AND METHOD FOR SPINE FIXATION

CROSS REFERENCE TO RELATED CO-PENDING APPLICATIONS

This application claims the benefit of U.S. provisional application Ser. No. 60/832,468 filed Jul. 21, 2006 and entitled "SYSTEM AND METHOD FOR FACET FIXATION", the contents of which are expressly incorporated herein by reference.

FIELD OF THE INVENTION

The present invention relates to a system and a method for spine fixation, and more particularly to a spine fixation system and a method utilizing a spine fixation assembly including pivoting guide wires and an angular guide system for positioning the guide wires.

BACKGROUND OF THE INVENTION

The human spine consists of individual vertebras that are connected to each other. Under normal circumstances the structures that make up the spine function to protect the neural structures and to allow us to stand erect, bear axial loads, and be flexible for bending and rotation. However, disorders of the spine occur when one or more of these spine structures are abnormal. In these pathologic circumstances, surgery may be tried to restore the spine to normal, achieve stability, protect the neural structures, or to relief the patient of discomfort. The goal of spine surgery for a multitude of spinal disorders especially those causing compression of the neural structures is often decompression of the neural elements and/or fusion of adjacent vertebral segments. Fusion works well because it stops pain due to movement at the facet joints or intervertebral discs, holds the spine in place after correcting deformity, and prevents instability and or deformity of the spine after spine procedures such as discectomies, laminectomies or corpectomies. Discectomy and fusion or corpectomy and fusion are most commonly performed in the cervical spine but there is increasing application in the thoracic and lumbar spine, as well.

Several spinal fixation systems exist for stabilizing the spine so that bony fusion is achieved. The majority of these fixation systems utilize fixation elements such as rods wires or plates that attach to screws threaded into the vertebral bodies, facets or the pedicles. Because the outer surface of the vertebral body is typically non-planer and the structure of the vertebras is relatively complex, it is important that the fixation elements (e.g., rods, plates, wires, staples and/or screws) are properly aligned when they are inserted into the vertebras. Improper alignment may result in improper or unstable placement of the fixation element and/or disengagement of the fixation element. However, achieving and maintaining accurate positioning and guidance of these fixation elements has proven to be quite difficult in practice. Such positioning difficulties are further complicated by the fact that the alignment angle for a fixation device through one vertebral body or pair of vertebral bodies will be unique to that individual due to individual differences in the spinal curvature and anatomies. Accordingly, there is a need for a method and a system for angular guiding and placing of spinal fixation elements.

SUMMARY OF THE INVENTION

In general, in one aspect, the invention features a method for attaching first and second fixation elements at a predetermined angle relative to each other to first and second locations of a vertebra, respectively. The method includes inserting a first guide wire into the first location of the vertebra, then inserting a first guide arm of an angular guide system over the first guide wire, then setting a second guide arm of the angular guide system at the predetermined angle relative to the first guide arm and then inserting a second guide wire through the second guide arm into the second location of the vertebra. The second guide wire comprises first and second members configured to pivot relative to each other and the method further includes pivoting the first member of the second guide wire out of the plane of the first guide wire while the second member of the second guide wire remains positioned into the second location. Next, dilating tissue around the first guide wire and inserting and attaching the first fixation element into the first location of the vertebra. Next, pivoting the first member back into the plane of the first guide wire and then dilating tissue around the second guide wire and inserting and attaching the second fixation element into the second vertebra location.

Implementations of this aspect of the invention may include one or more of the following features. The first and second locations may be facet joints, pedicles, transverse processes, pars, lamina, vertebral body, sacrum, lateral mass, or occiput locations. The tissue dilating comprises inserting a dilator over the first guide wire and the dilator includes an outer dilator cannula and an inner dilator configured to move within the outer dilator cannula and to dilate the tissue. The method further includes drilling into the first location prior to the inserting and attaching of the first fixation element. The drilling is performed with a drill having adjustable drill depth and an automatic drill stop. The first fixation element is inserted and attached to the first location with a driver having a fixation element retaining and releasing mechanism. The fixation element may be screw having an elongated body having a threaded portion at a distal end and a head at a proximal end and a washer configured to be positioned at an angle relative to the head. The washer comprises a bottom surface having protrusions configured to engage the first location. The protrusions may be spikes, teeth, serrations, grooves, or ridges.

In general in another aspect the invention features a system for attaching first and second fixation elements at a predetermined angle relative to each other to first and second locations of a vertebra, respectively. The system includes a first guide wire configured to be inserted into the first location of the vertebra, an angular guide system comprising first and second guide arms configured to be set at the predetermined angle relative to each other and the first guide arm is configured to be inserted over the first guide wire and a second guide wire configured to be inserted through the second guide arm into the second location of the vertebra. The second guide wire includes first and second members configured to pivot relative to each other.

Among the advantages of this invention may be one or more of the following. The system allows the fixation elements to be implanted and removed one piece at a time via minimally invasive surgery. The angular positioning of the fixation elements relative to each other reduces the need for repeated fluoroscopy imaging which reduces the surgery time and the radiation exposure of the patient.

BRIEF DESCRIPTION OF THE DRAWINGS

Referring to the figures, wherein like numerals represent like parts throughout the several views.

DETAILED DESCRIPTION OF THE INVENTION

Figure 1:
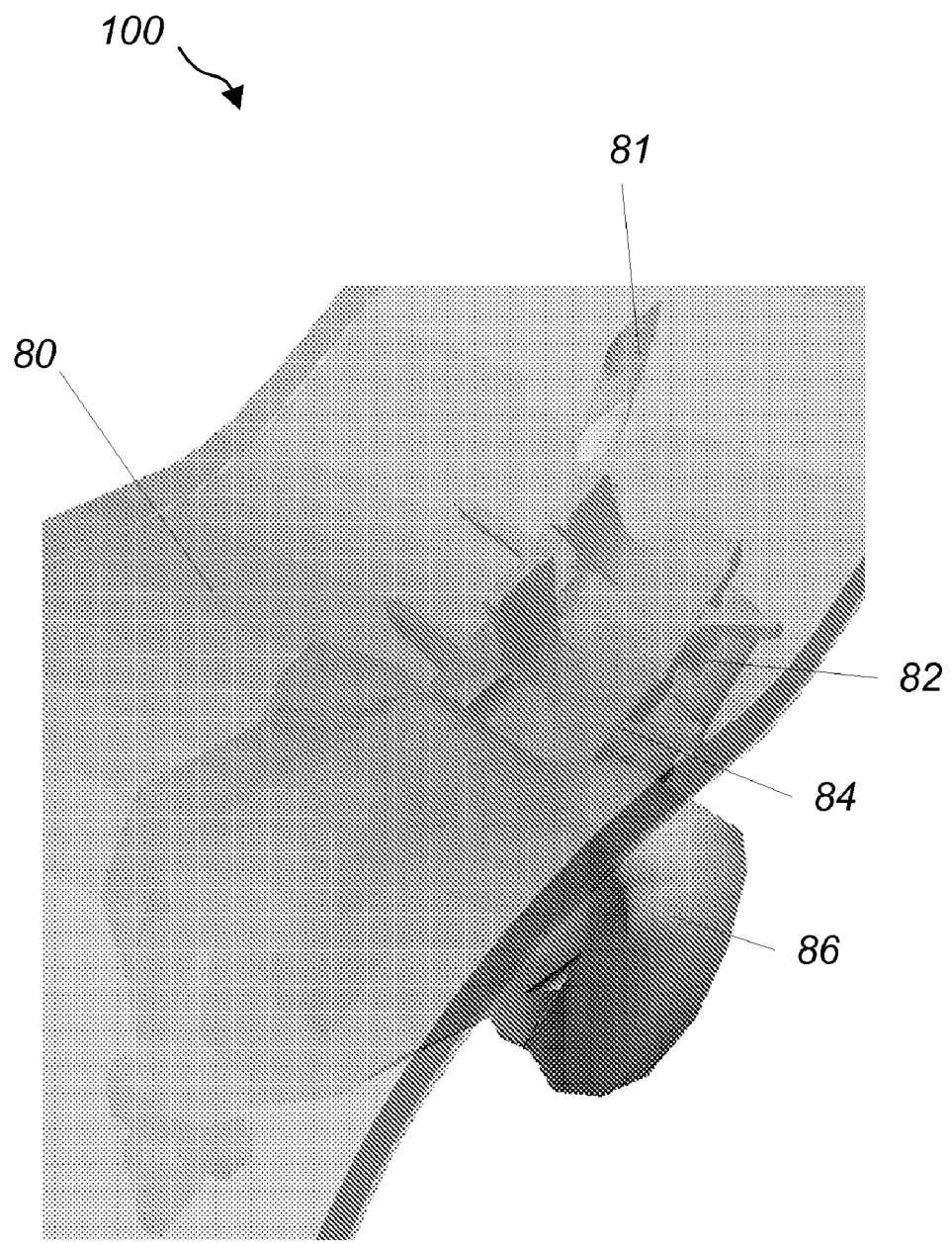
FIG. 1 is a schematic posterior view of a patient's lower back.
Figure 2:
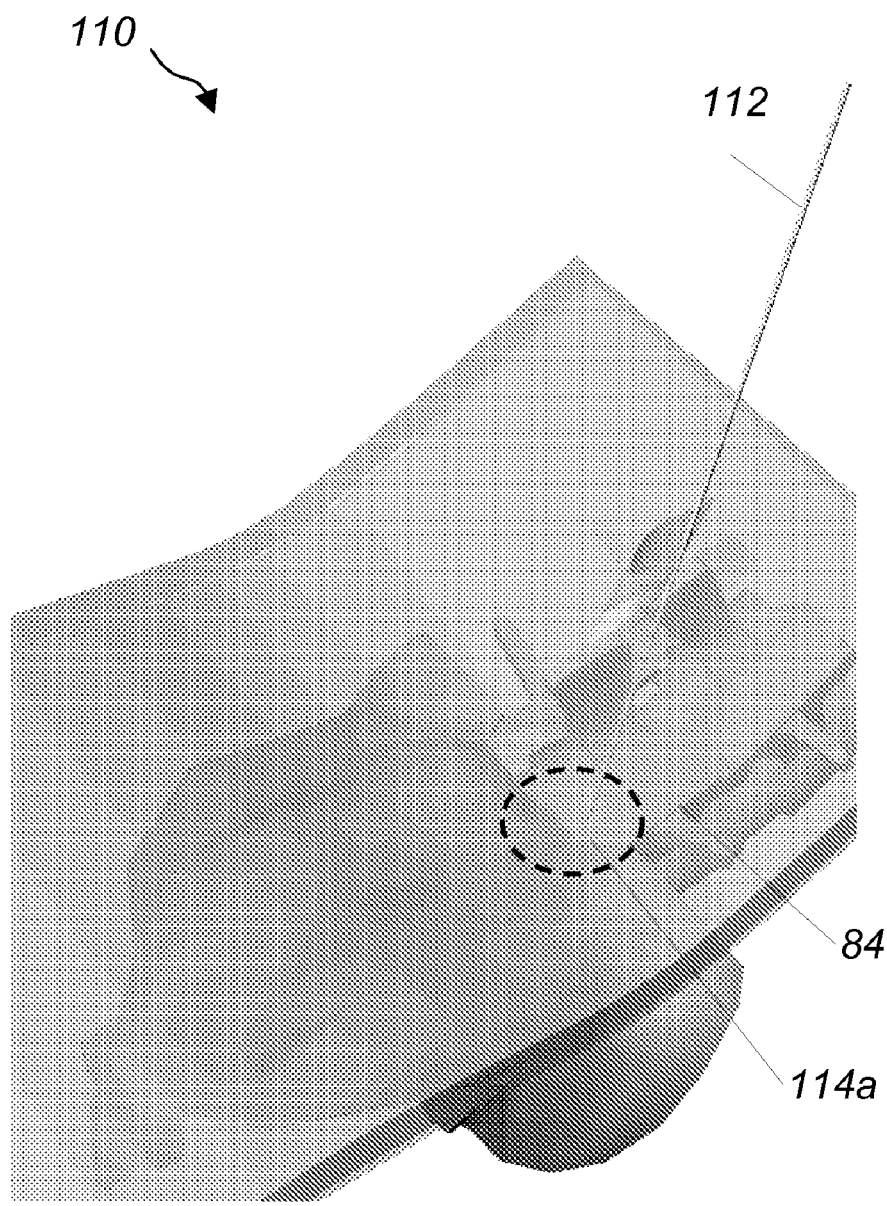
FIG. 2 depicts inserting a first guide wire into the patient's back of FIG.1.
Figure 3:
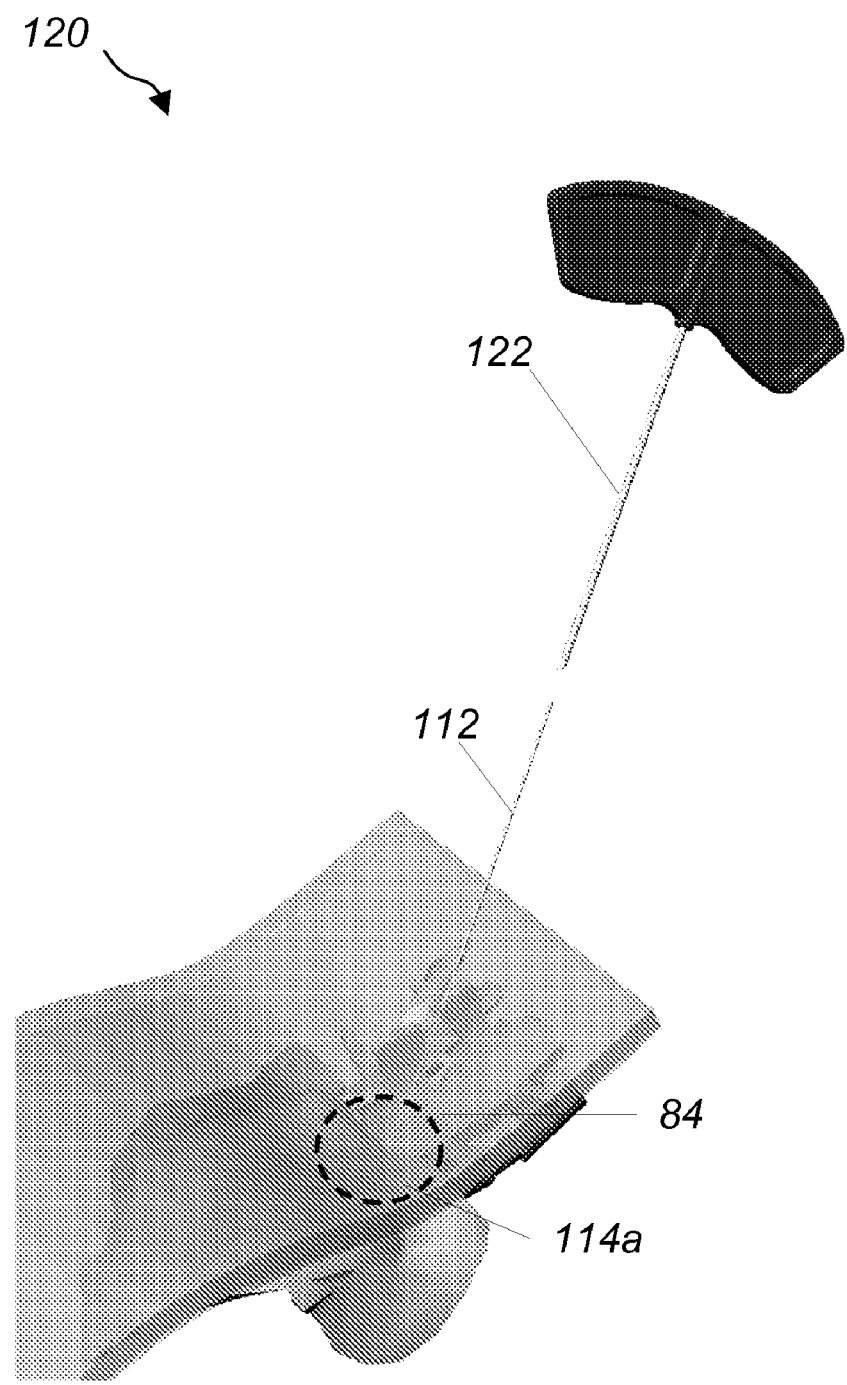
FIG. 3 depicts inserting a bone needle over the first guide wire of FIG.2.
Figure 4:
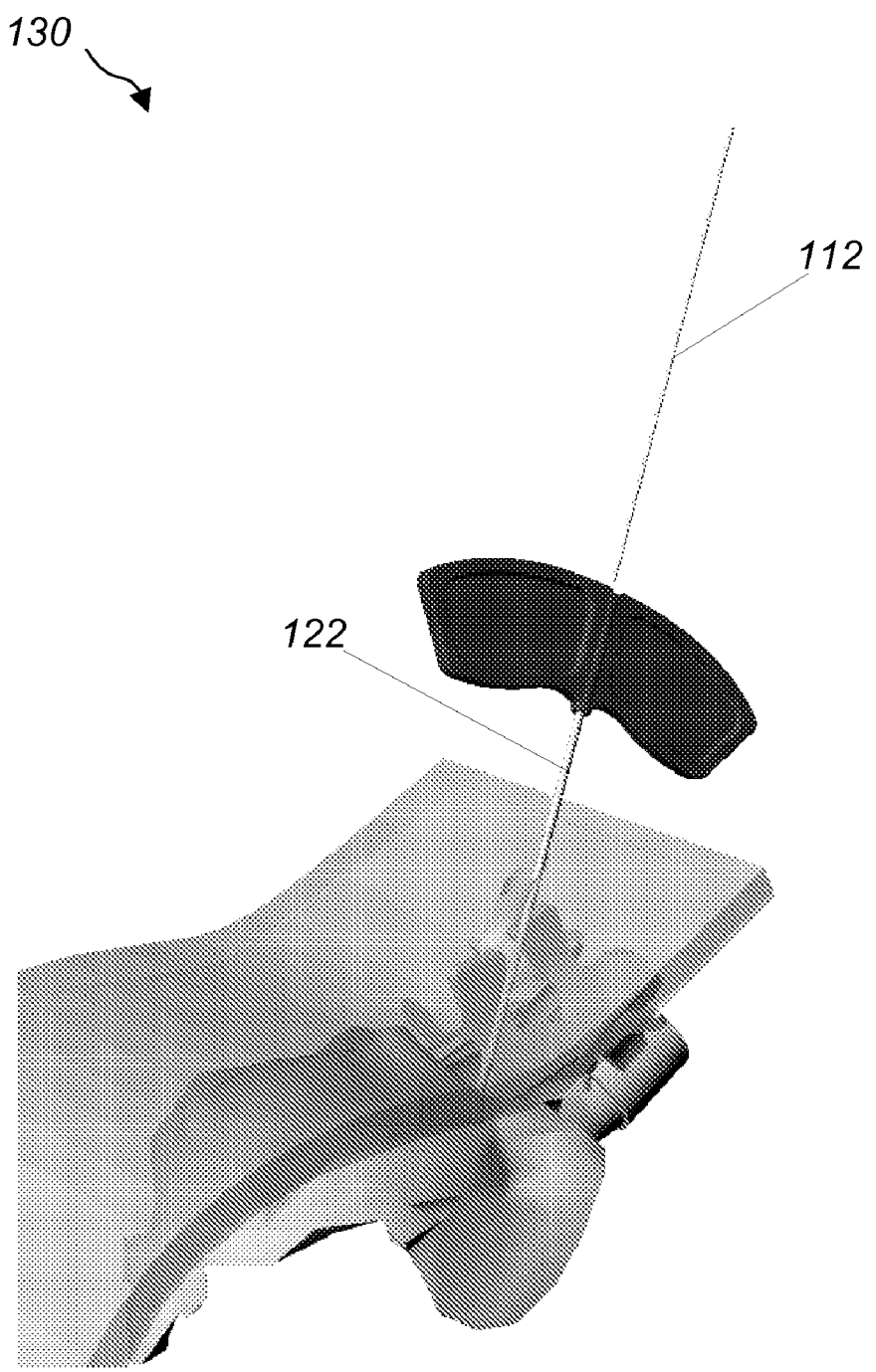
FIG. 4 depicts tapping the bone with the bone needle of FIG. 3.
Figure 5:
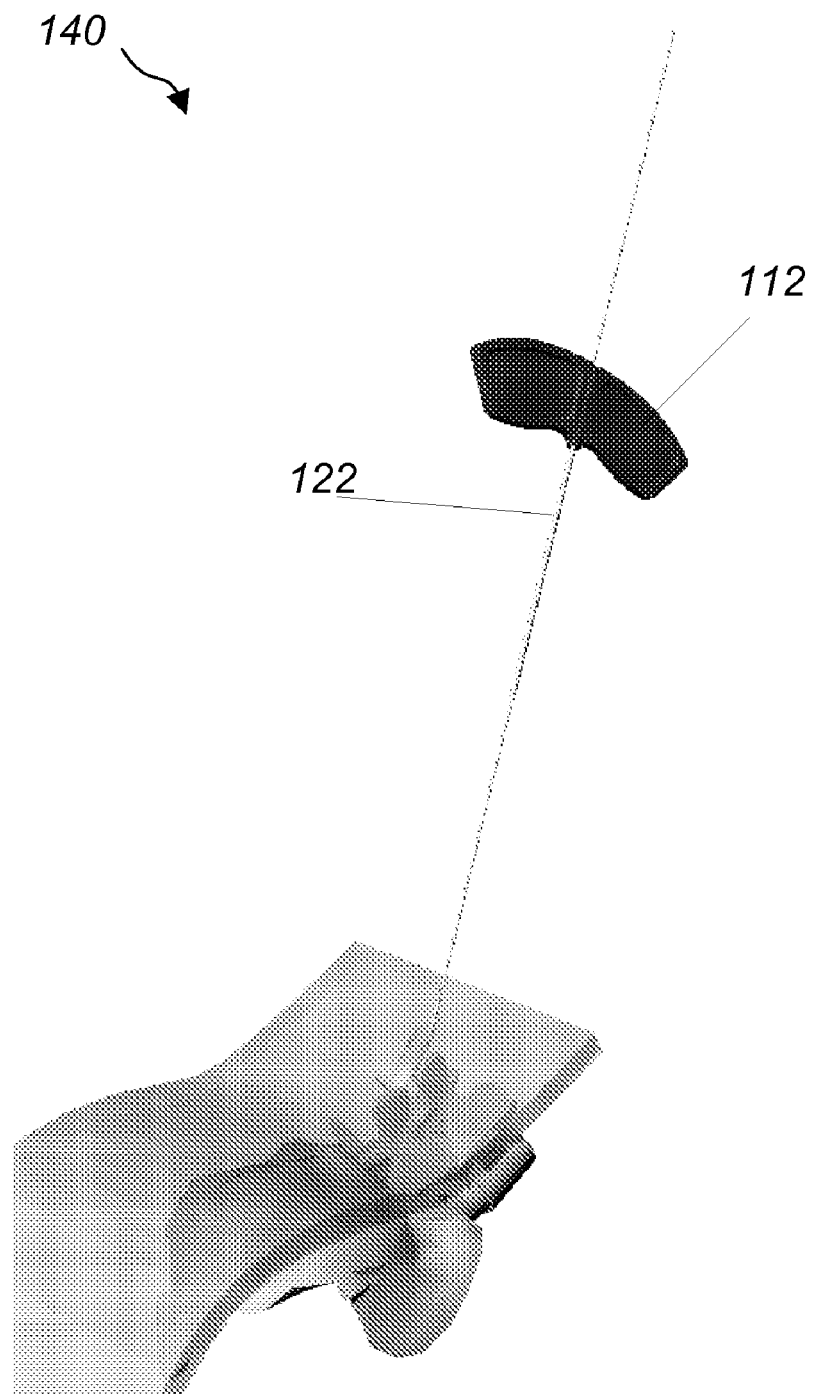
FIG. 5 depicts removing the bone needle.
Figure 6:
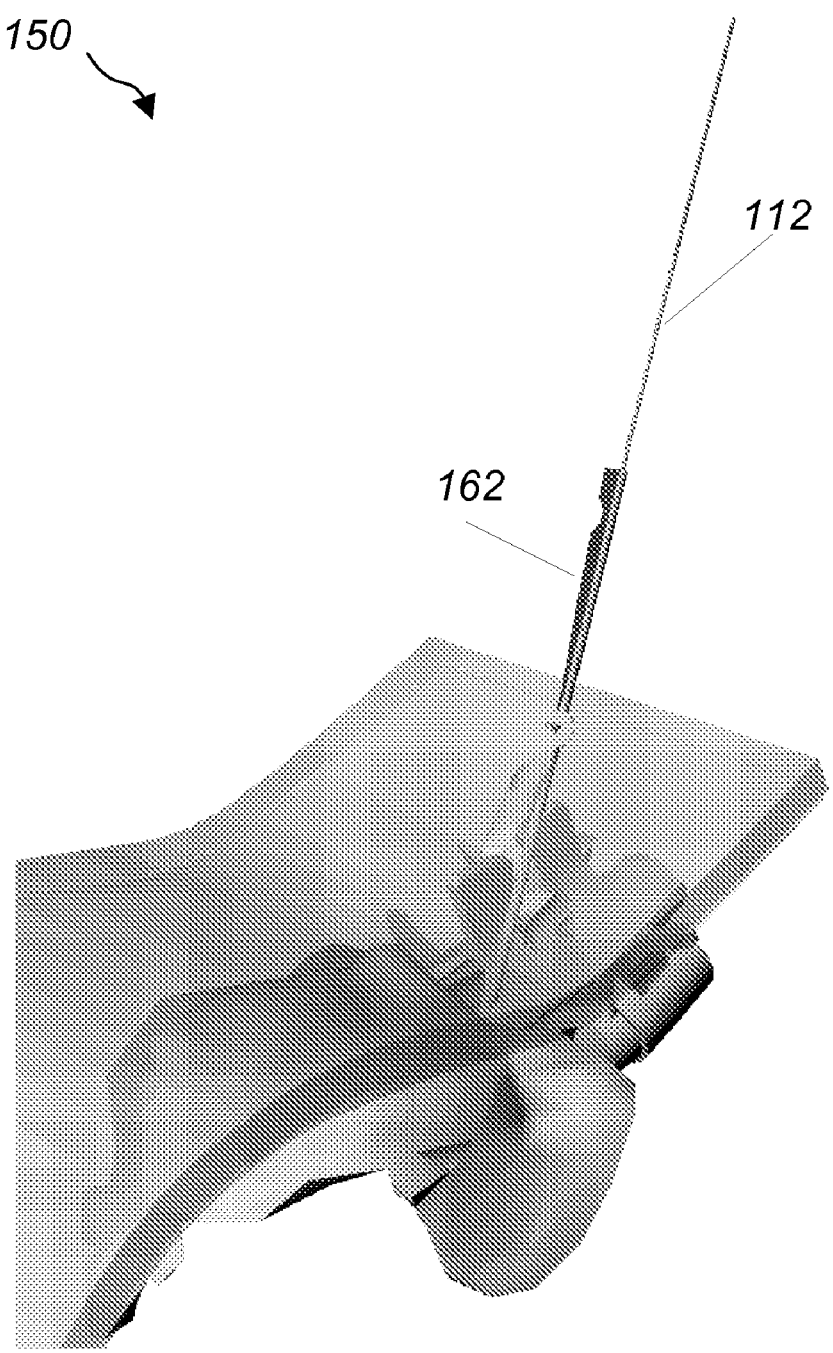
FIG. 6 depicts inserting the first guide member over the first guide wire of FIG. 5.
Figure 7:
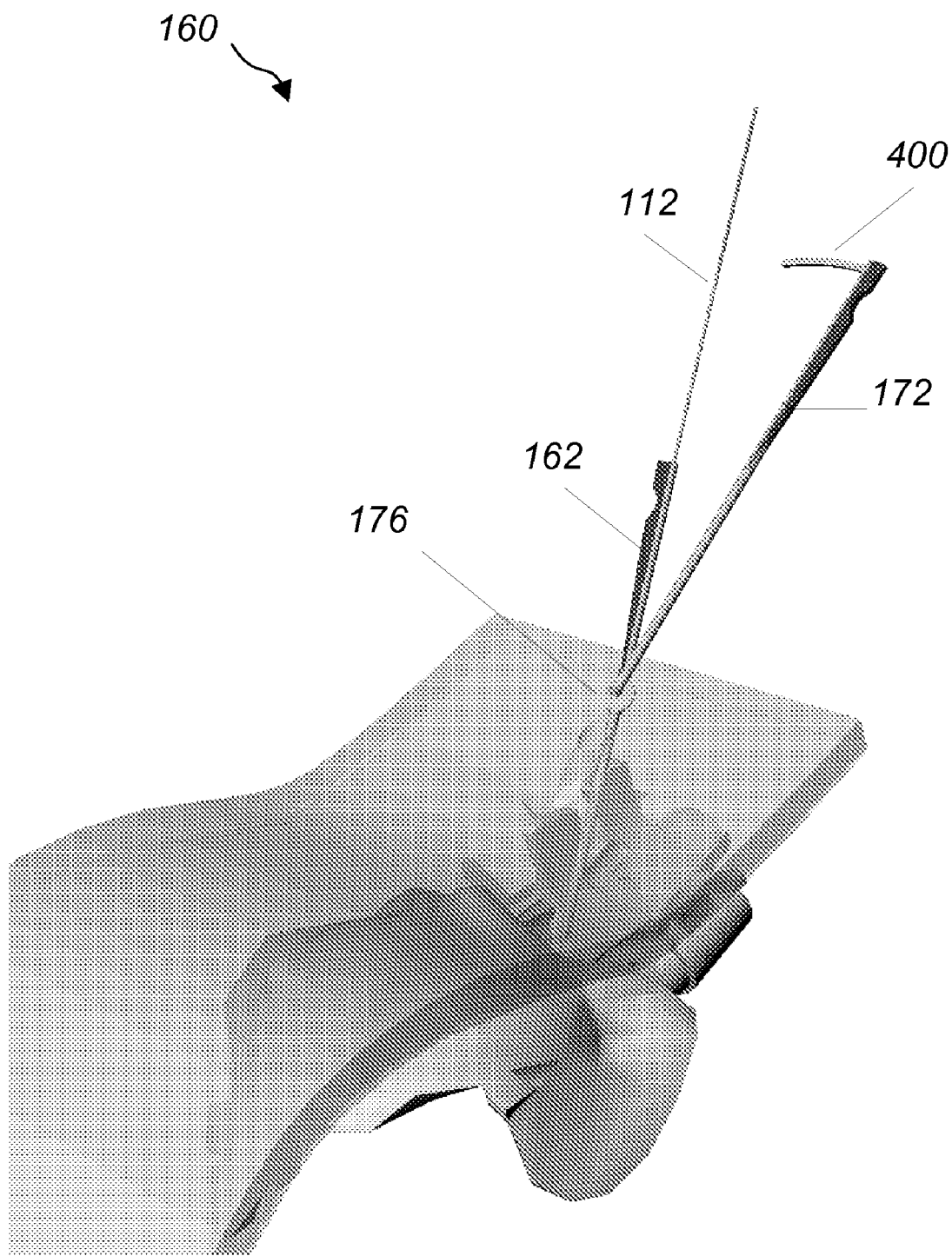
FIG. 7 depicts connecting the second guide member to the first guide member of FIG. 6.
Figure 8:
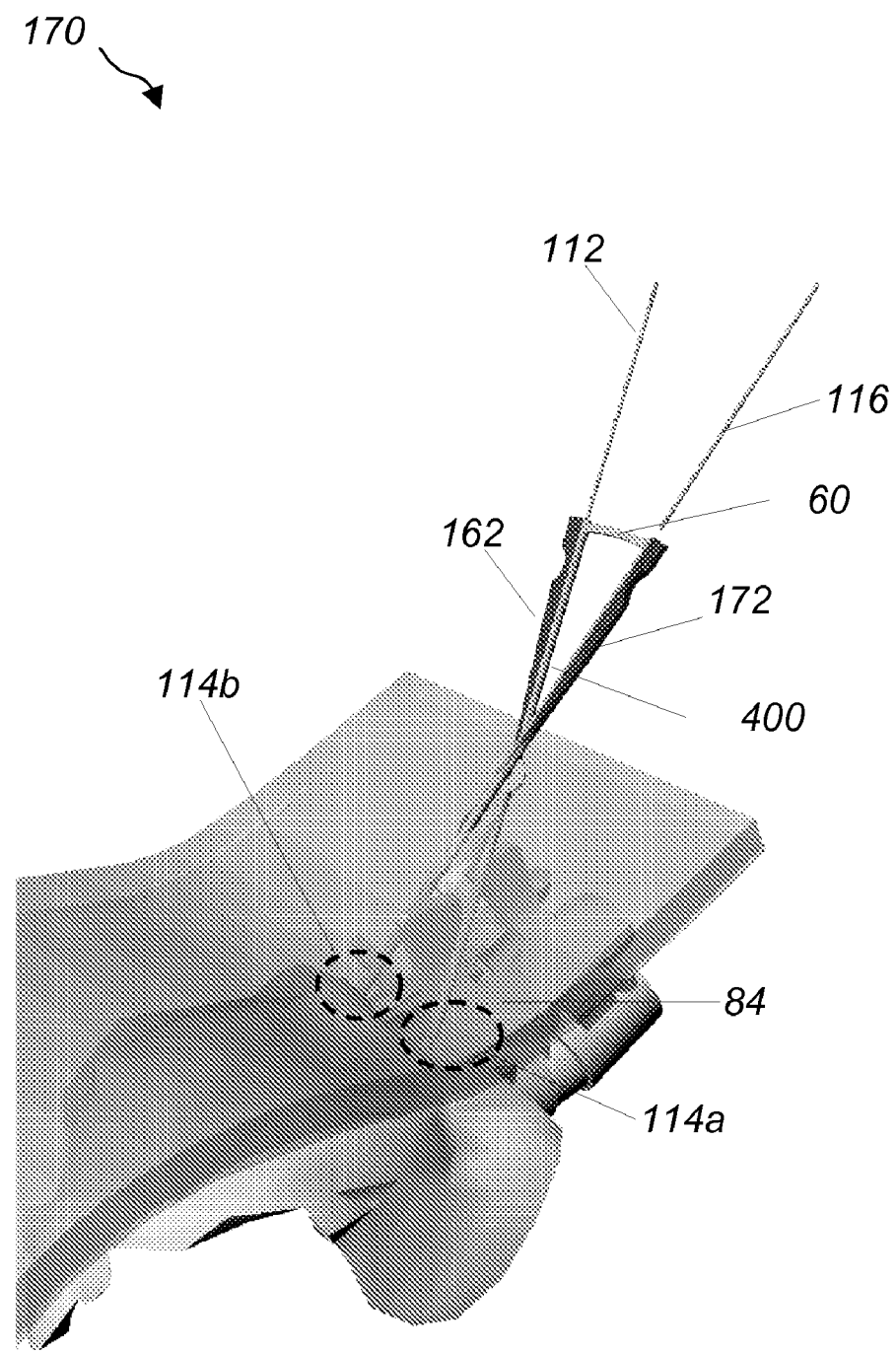
FIG. 8 depicts setting the angle between the first and second guide members and inserting a second guide wire through the second guide member into the patient's back.
Figure 9:
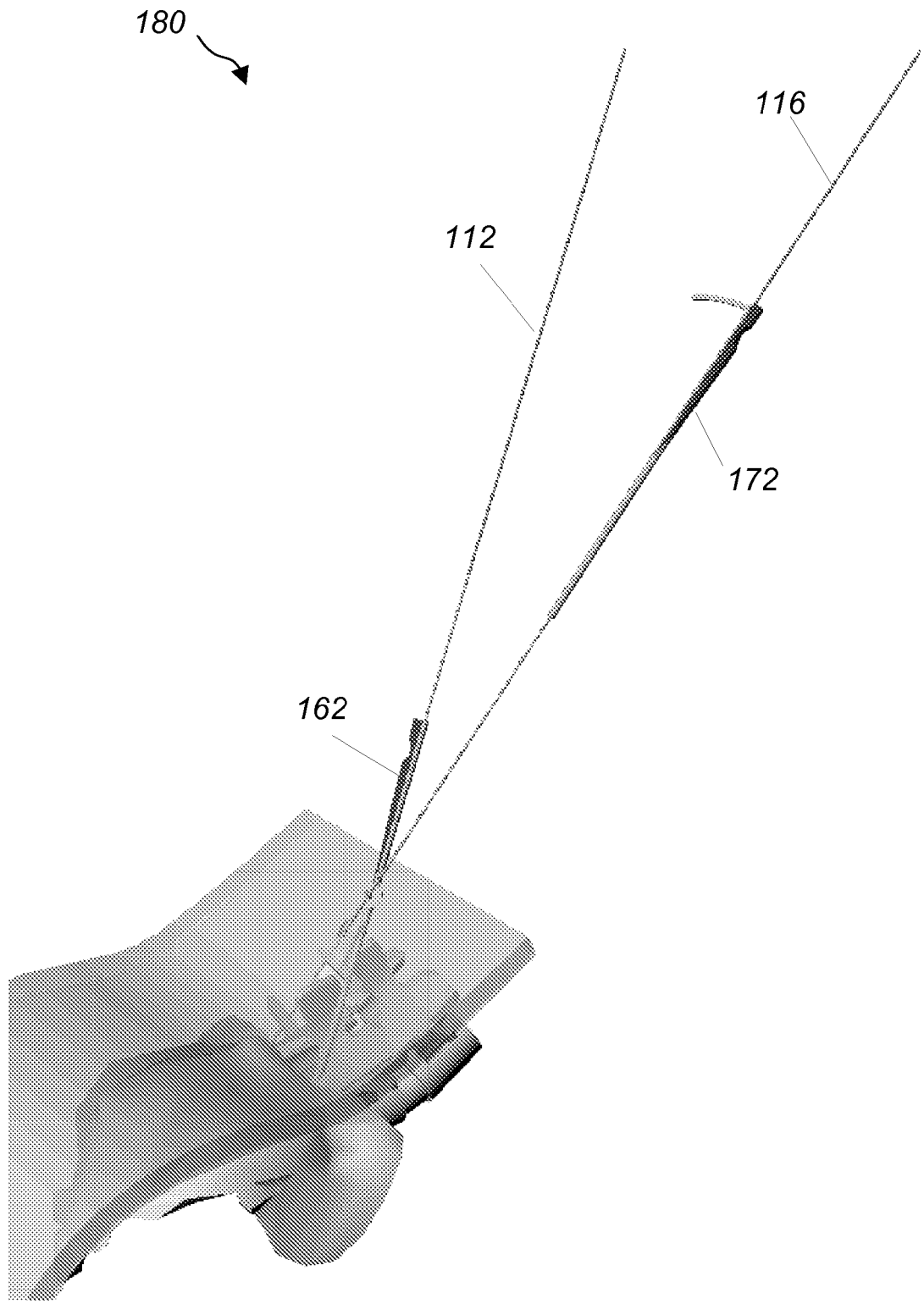
FIG. 9 depicts removing the second guide member.
Figure 10:
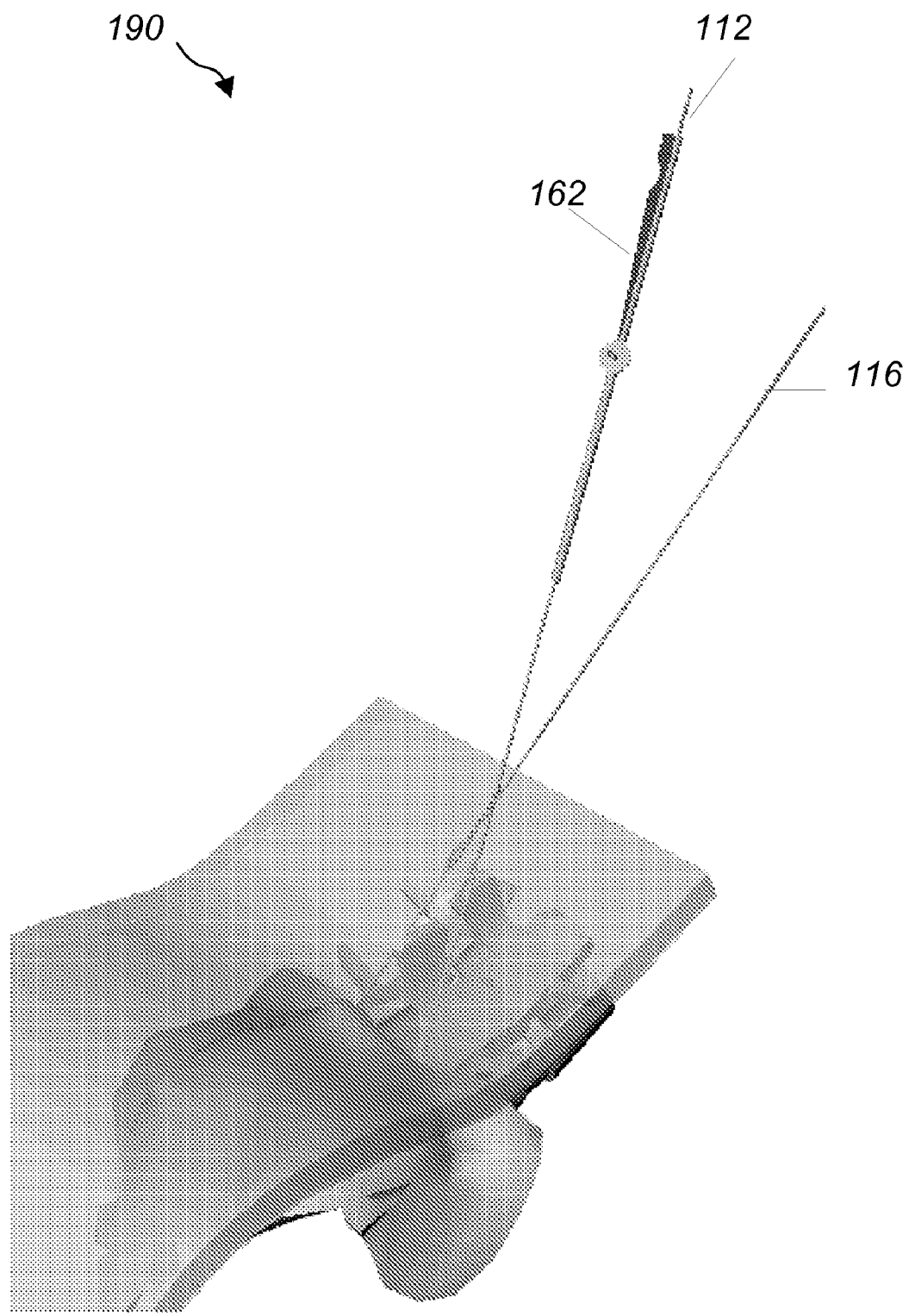
FIG. 10 depicts removing the first guide member.

Referring to FIG. 1-FIG. 19 a new method for facet fixation includes the following steps. First, patient 80 is positioned prone, lying flat on an operating table in preparation for a minimally invasive surgery (MIS) (100). Next, location 114a corresponding to a first facet joint of the L5 lumbar vertebra 84, is radiographically identified and marked on the patient's lower back. For MIS procedures, a skin incision 81 is performed and a first guide wire 112 is inserted in the facet joint location 114a (110). The placement of the guide wire 112 is verified by taking a fluoroscopic image of the patient's back. The fluoroscopic image is further used to identify the location of the facet joints 114a, 114b of vertebra 84 and the angular relationship between them. Guide wire 112 or Kirschner wire (also called K-wire) is a thin, rigid wire that is used to stabilize bone fragments in orthopedics and other types of medical and veterinary surgery. Kirschner wires were introduced in surgical procedures by Martin Kirschner in 1909. They are sterilized, sharpened, smooth stainless steel pins and have different sizes. These wires can be drilled through the bone to hold bone fragments in place. They are placed percutaneously (through the skin), thus avoiding an operation in some cases. In other cases, the K-wires are used after an operation to hold bone fragments in place. In some cases the K-wires include threads for threading into the bone. In spine surgery K-wires are used as guide wires for the placement of spine fixation components, such as screws and pins. They are inserted either through an open surgical procedure or under fluoroscopic or X-ray observation and are removed after the insertion of the screws. In one example guide wire 112 is a threaded 140 millimeter K-wire, manufacture by SpineFrontier, Inc (Beverly, Mass.).

Figure 11:
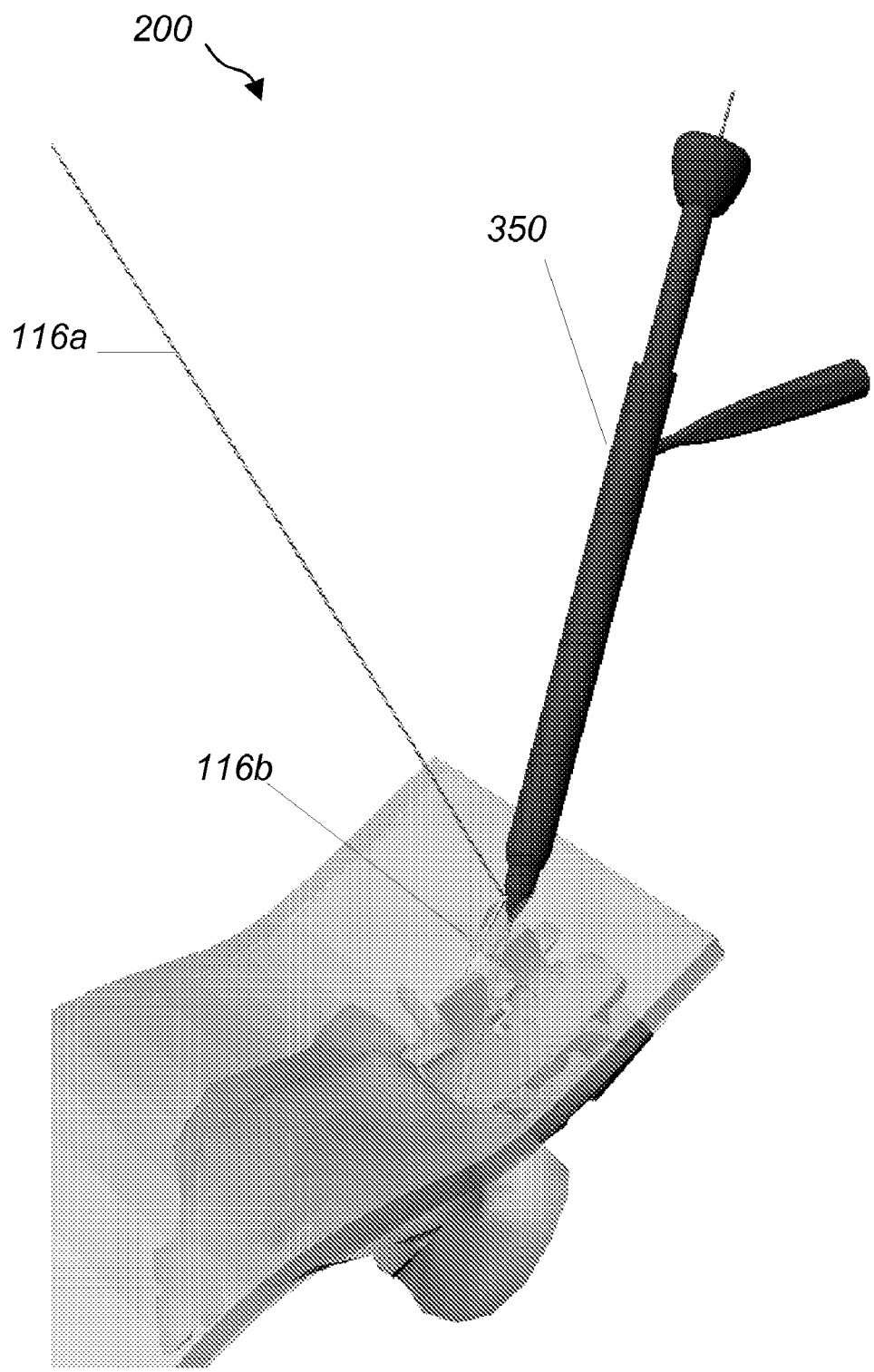
FIG. 11 depicts inserting a tissue dilator into over the first guide wire.
Figure 12:
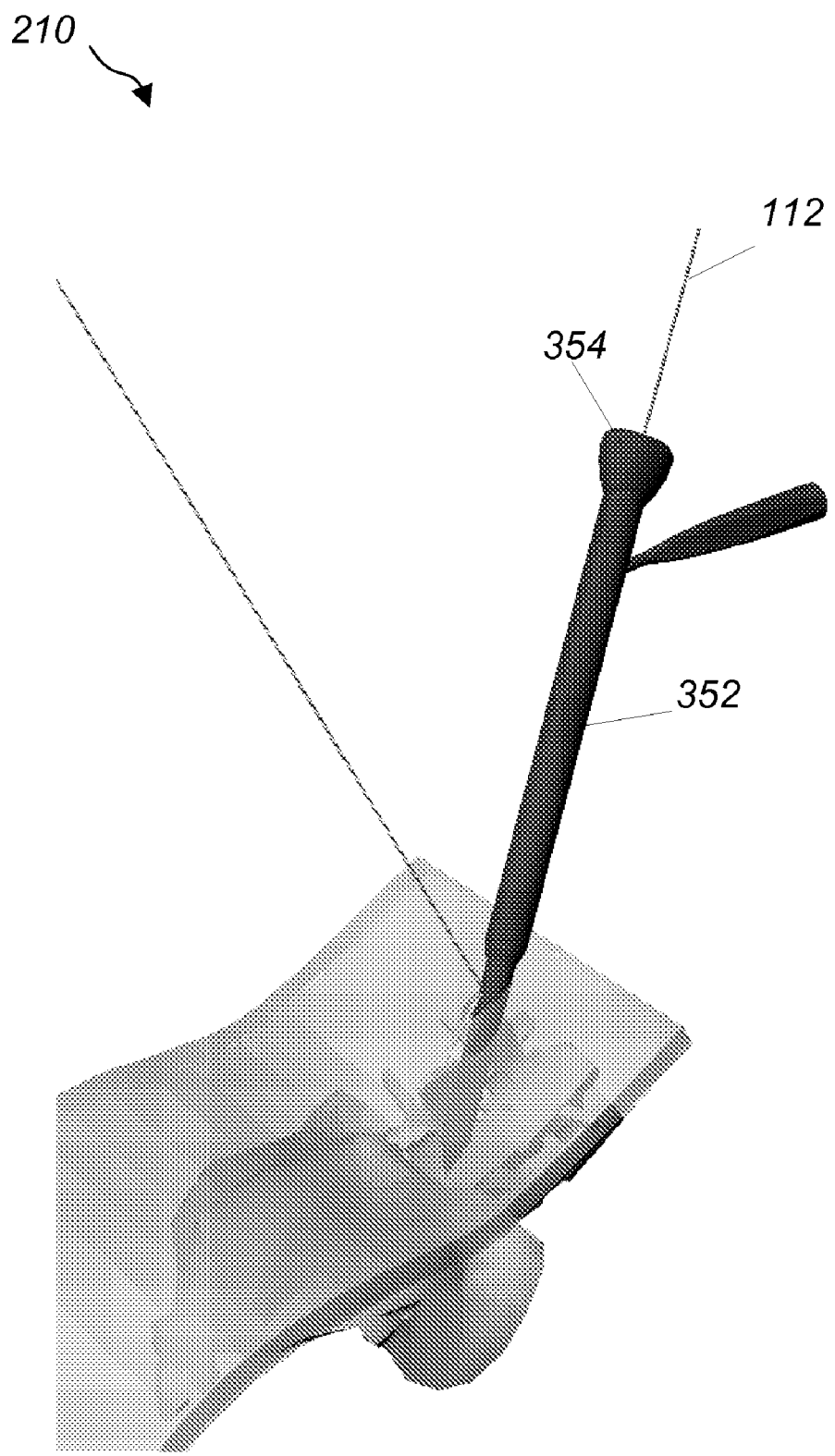
FIG. 12 depicts dilating the tissue around the first guide wire.
Figure 13:
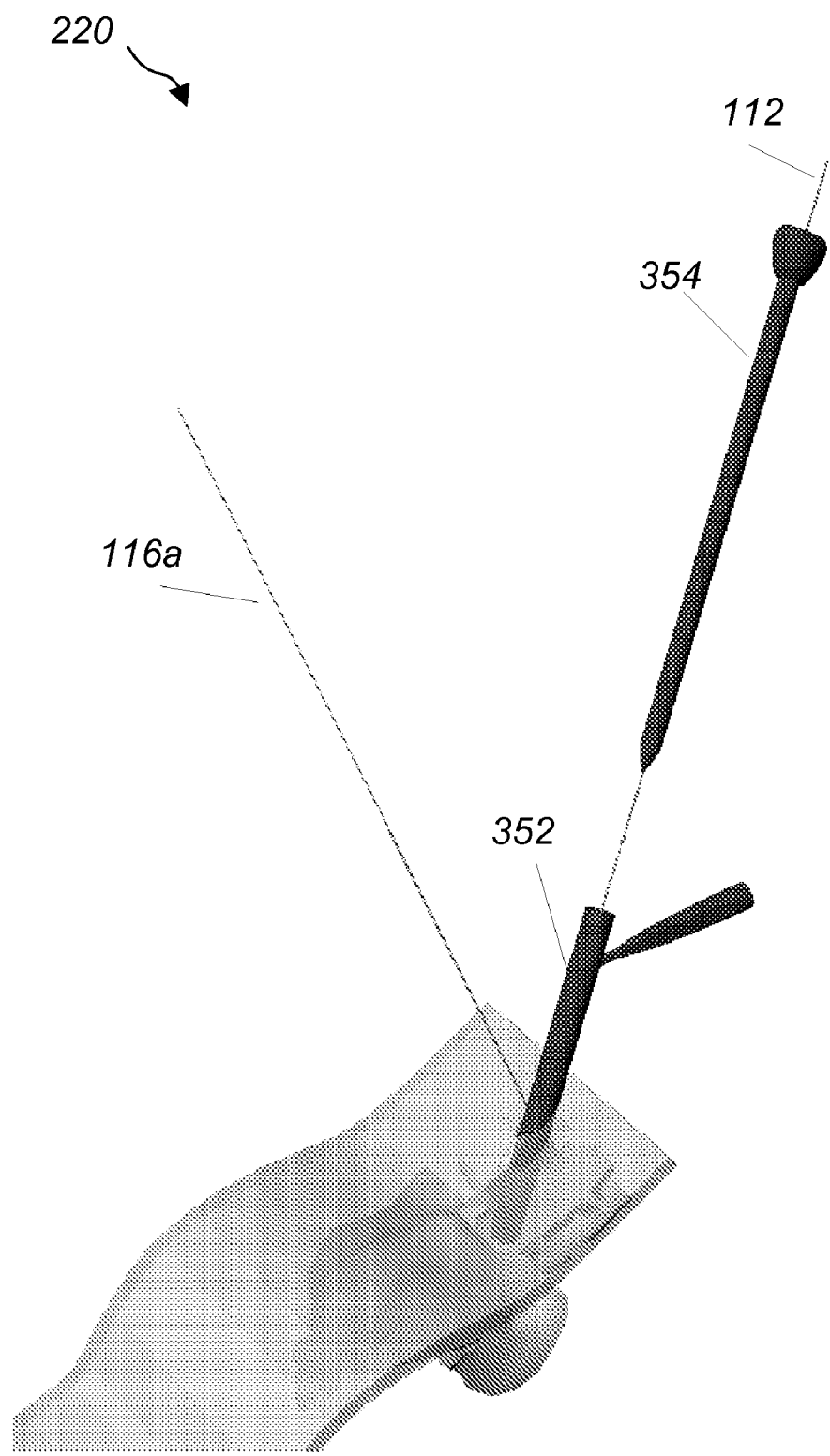
FIG. 13 depicts removing the inner dilator member.
Figure 14:
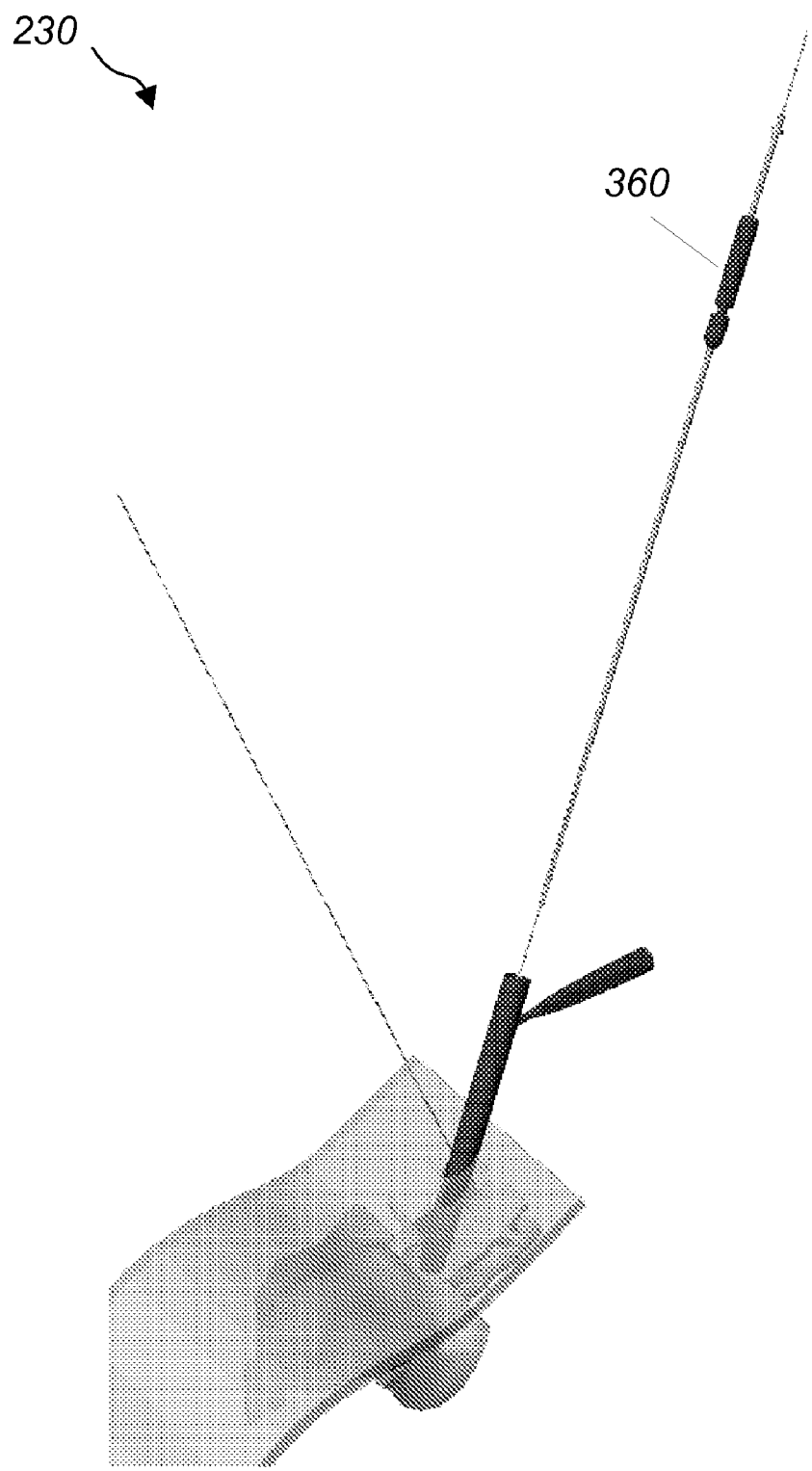
FIG. 14 depicts inserting a drill into the outer dilator member.
Figure 15:
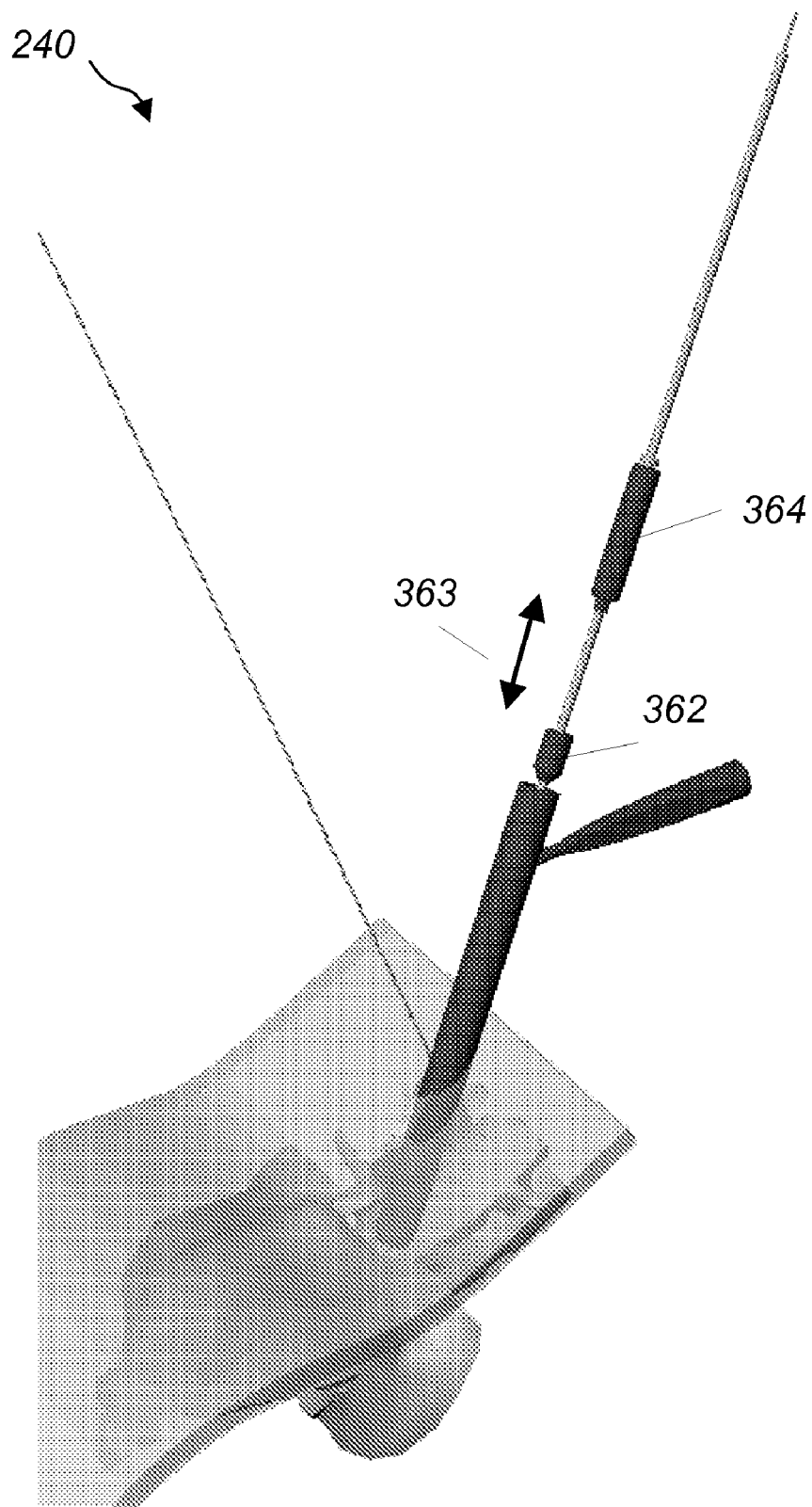
FIG. 15 depicts drilling into the bone around the first guide wire.
Figure 16:
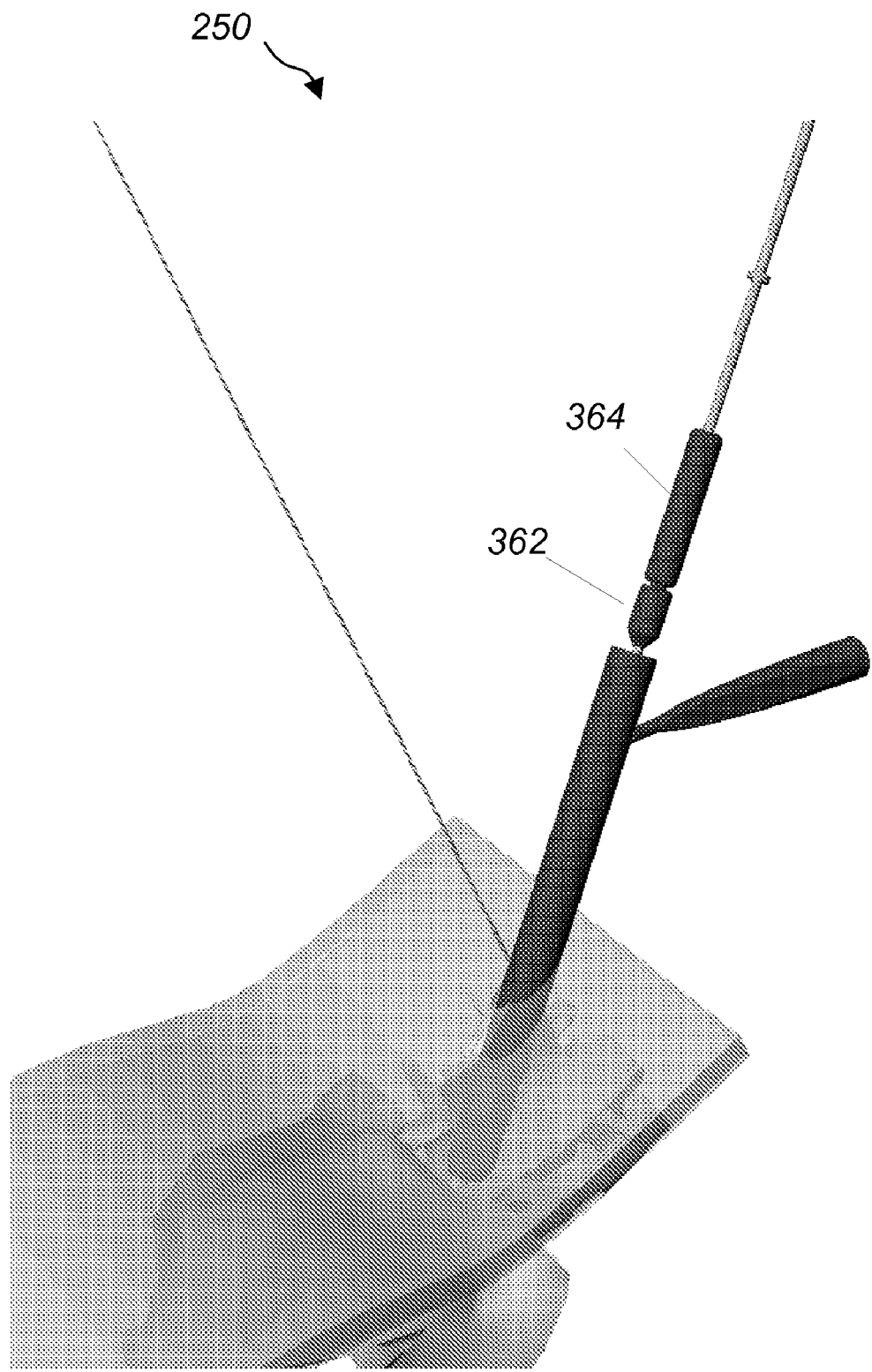
FIG. 16 depicts the automatic stopping mechanism of the drilling process.
Figure 17:
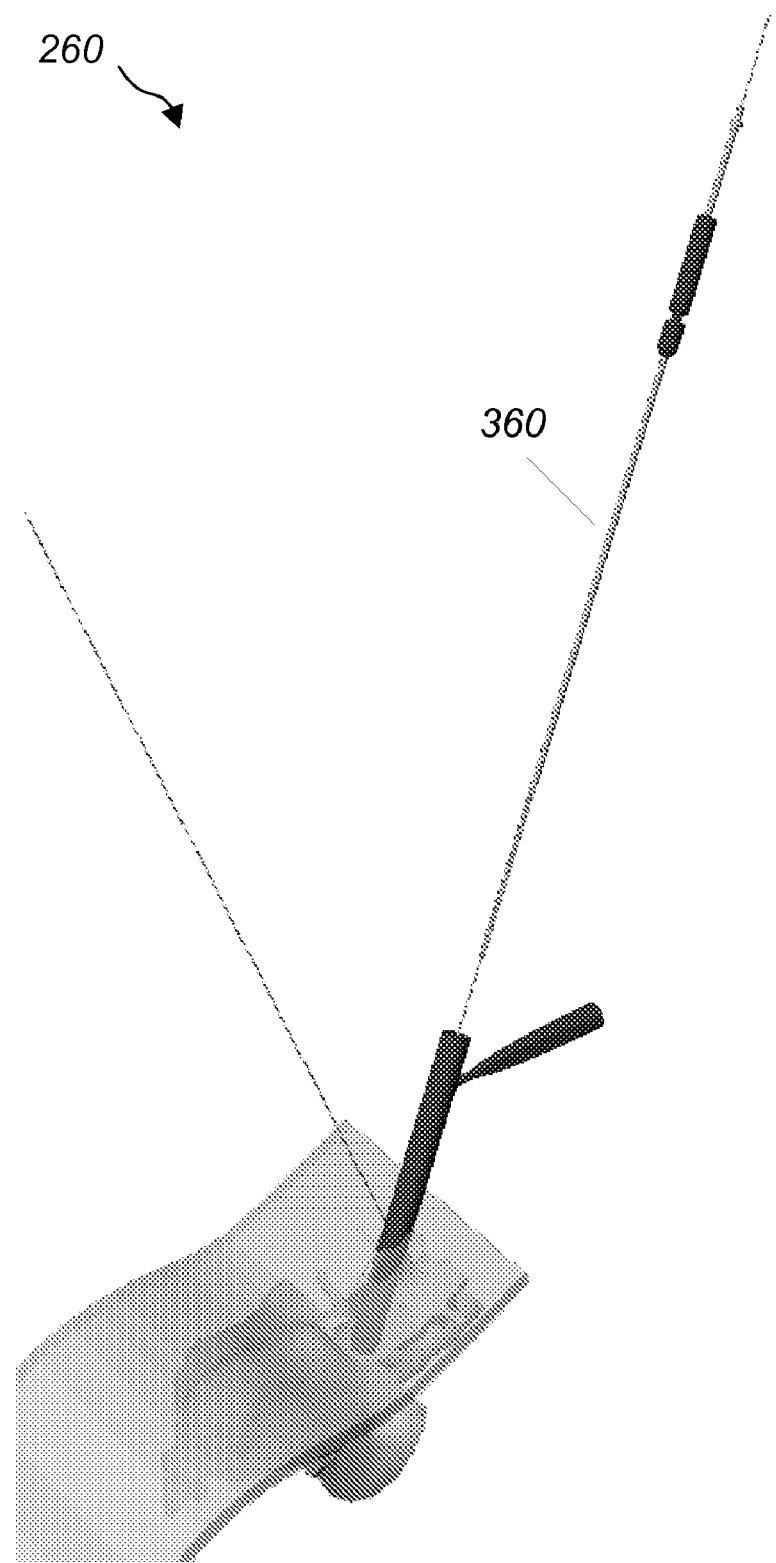
FIG. 17 depicts removing the drill.
Figure 18:
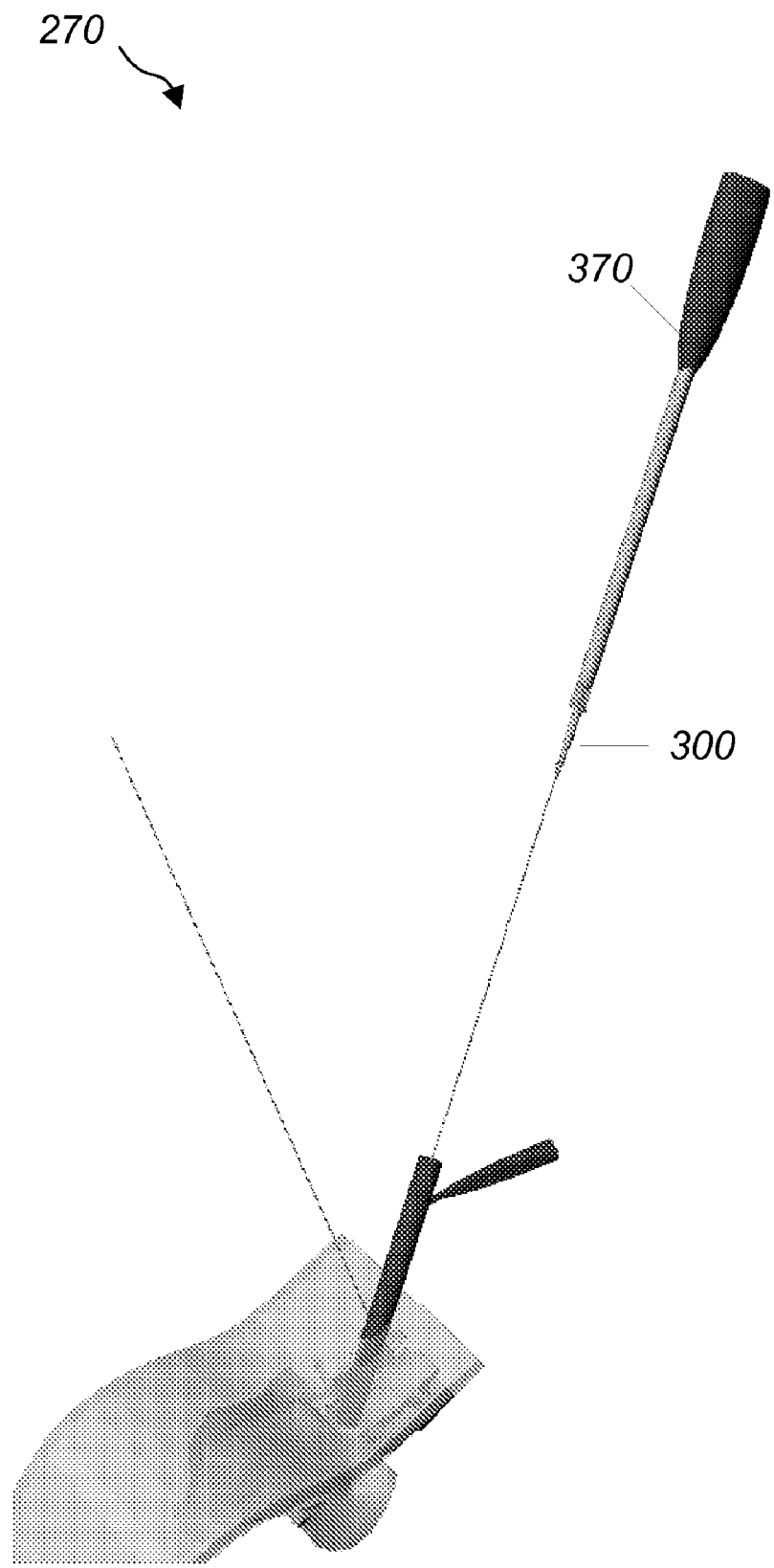
FIG. 18 depicts inserting a first facet screw into the opening over the first guide wire.
Figure 19:
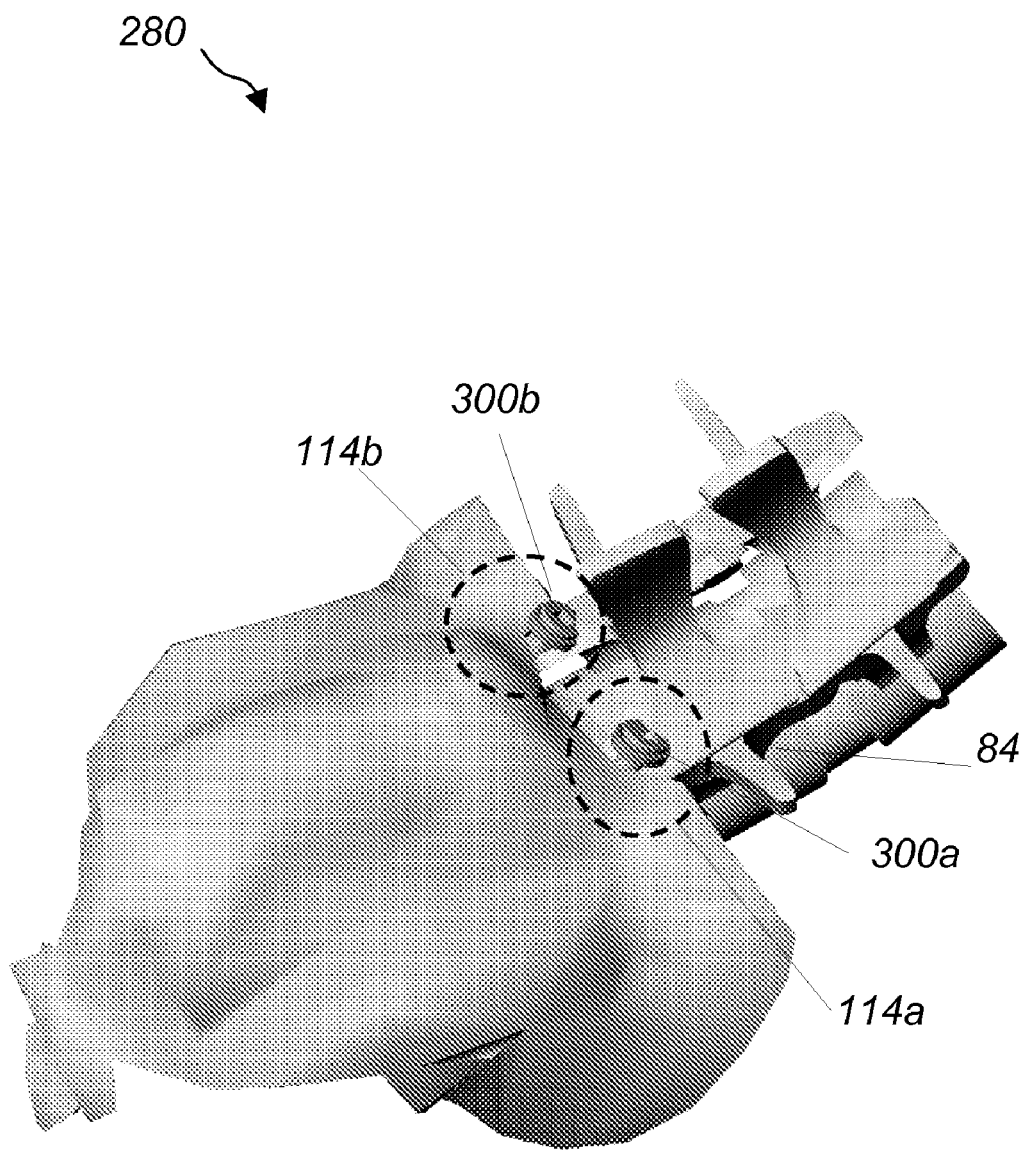
FIG. 19 is a schematic diagram of the lower vertebra with the installed facet screws.
Figure 20:
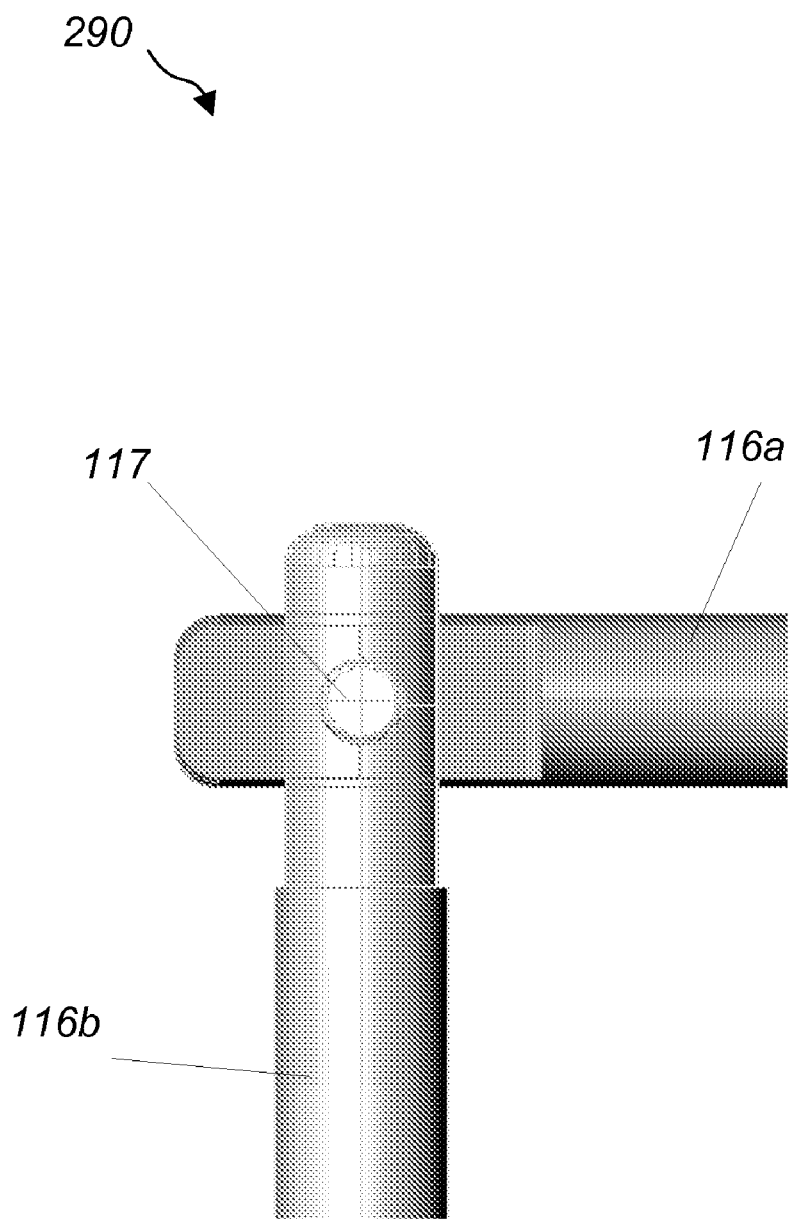
FIG. 20 is a schematic diagram of a pivoting guide wire.
Figure 24:
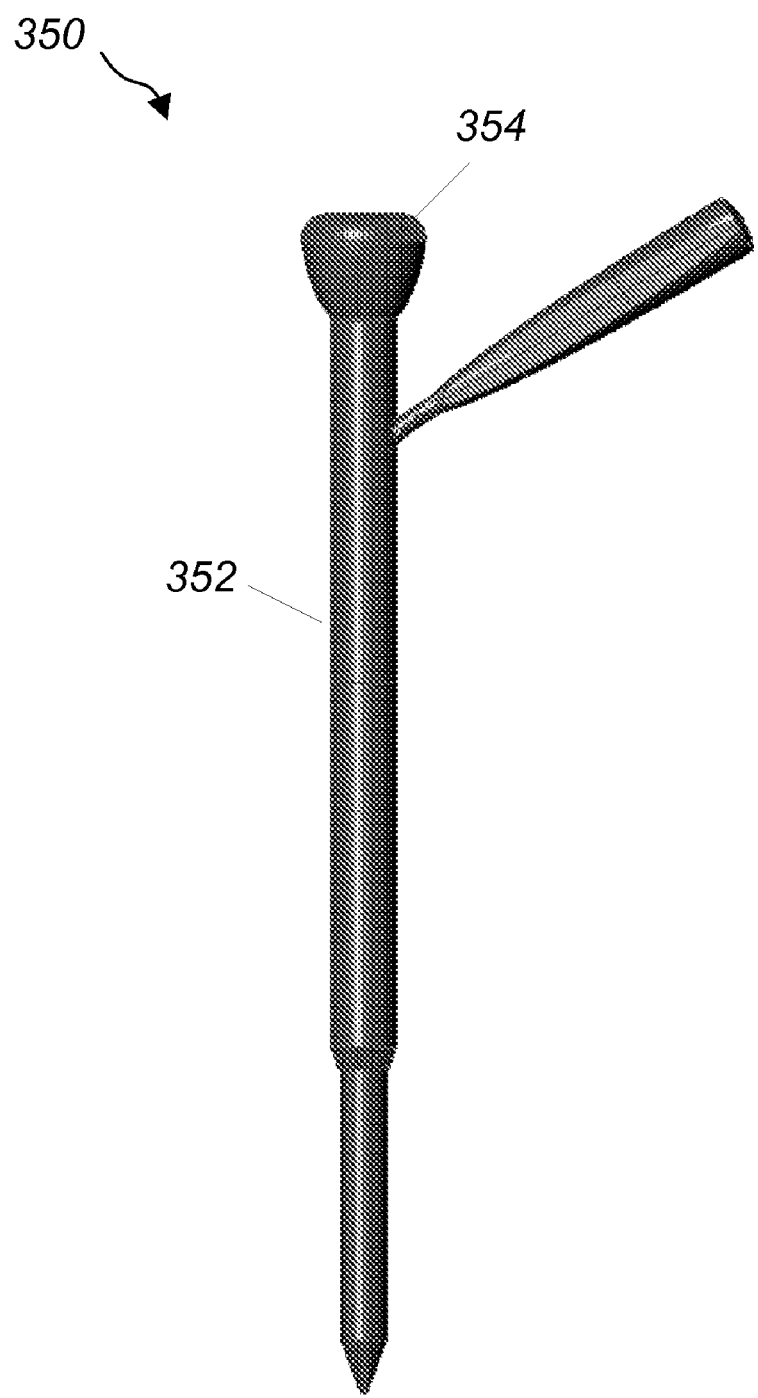
FIG. 24 is a front perspective view of the dilator of FIG. 11.
Figure 25:
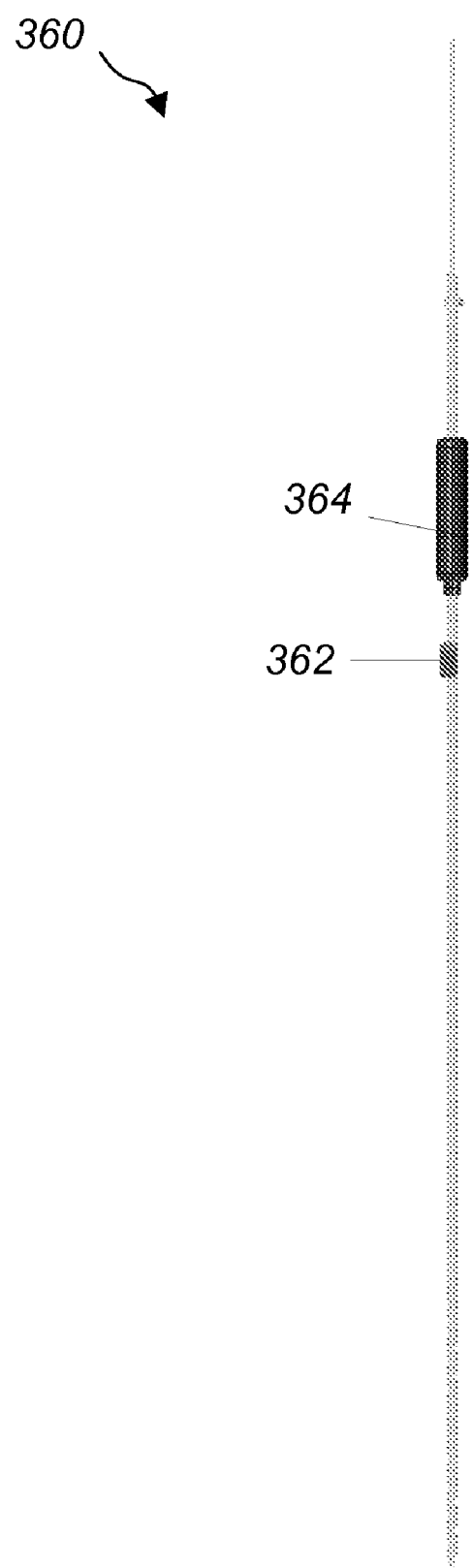
FIG. 25 is a front perspective view of the drill of FIG. 15.
Figure 26:
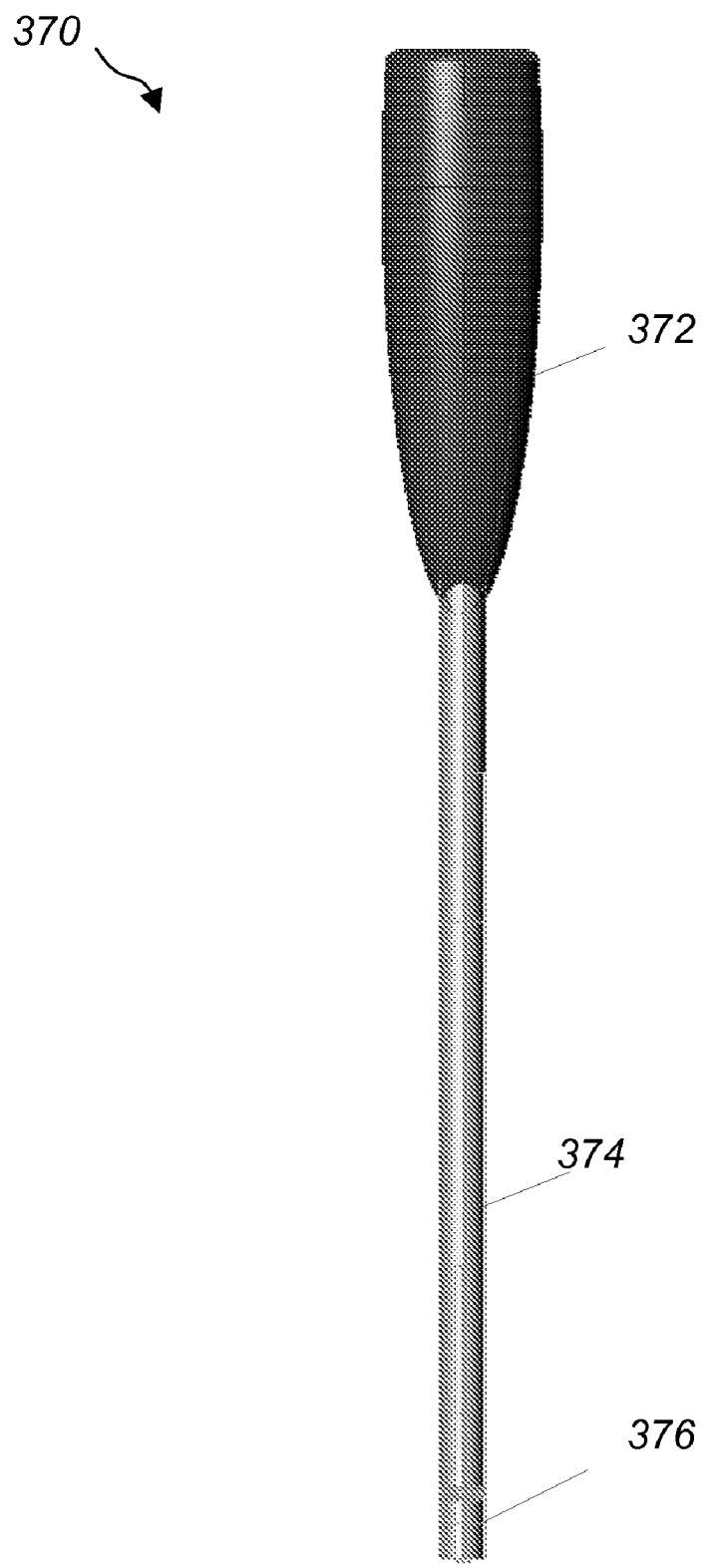
FIG. 26 is a front perspective view of the screwdriver of FIG. 18.

Next, a bone needle 122 is inserted over the guide wire 112 (120) and tapped into the facet joint 114a (130). I one example, bone needle 122 is a Jamshide bone needle, manufactured by Baxter-Allegiance. The bone needle is then removed (140), and first arm 162 of an X-guide tool 400 is inserted over the guide wire 112 (150). Second arm 172 of the X-guide tool 400 is connected to the first arm 162 at pivot point 176 (160) and the angle 60 between the two arms 162, 172 is set so that a second guide wire 116 inserted through the second arm will meet the location of the second facet joint 114b of vertebra 84. Angle 60 was determined from the fluoroscopic image of the patient's back, as was mentioned above. Second guide wire is then inserted through the second arm 172 of the X-guide tool 400 into the location of the second facet joint 114b (170). Second guide wire 116 includes two elongated members 116a, 116b pivotally connected at point 117, as shown in FIG. 20. In one example, guide wire 116 is a threaded 50 centimeter pivoting K-wire, manufacture by SpineFrontier, Inc (Beverly, Mass.) and the X-guide tool 400 is a two arm angular positioning guide manufactured also by SpineFrontier, Inc (Beverly, Mass.). Next, the two guide arms 172, 162 are removed (180), (190), and the upper arm 116a of the pivoting guide wire 116 is pivoted out of the plane of the first guide wire 112, as shown in FIG. 11 (200). A tissue dilator 350 is then inserted over the first guide wire 112 (200). Tissue dilator 350 include an outer dilator cannula 352 and an inner dilator 354 configured to slide within the outer dilator cannula 352, as shown in FIG. 24. In one example, tissue dilator 350 is a dilator manufactured by SpineFrontier, Inc (Beverly, Mass.). The inner dilator 354 is advanced within the outer dilator cannula and the tissue around the first guide wire 112 is dilated (210). Next the inner dilator 354 is removed and the outer dilator cannula 352 is advanced into the patient's tissue (220), as shown in FIG. 13. Next a hand drill 360 is inserted into the outer dilator cannula (230). Referring to FIG. 25, hand drill 360 has a handle 364 and an adjustable stop 362. The distance 363 between the drill stop 362 and handle 364 is adjusted to correspond to the length of the facet screw that need to be inserted into the facet joint 114a. Accordingly, in step 240 length 363 is adjusted to match the length 301 of the facet screw 21, shown in FIG. 21 and then the handle is advanced down until it hits the stop 362 (250). In one example, hand drill 360 is a drill manufactured by SpineFrontier, Inc (Beverly, Mass.). Next, the hand drill 360 is removed (260) and a screwdriver 370 with a removable attached screw 300 is inserted in the location 114a via the outer dilator cannula 354 (270). The screw 300 is attached to location 114a and the screwdriver 370 and the outer dilator cannula 354 are removed. Referring to FIG. 26, in one example screwdriver 370 has a removable screw attaching mechanism 376 and is manufactured by SpineFrontier, Inc (Beverly, Mass.).

Next, the upper arm 116a of the second guide wire 116 is straighten and the process of dilation, drilling and screw driving is repeated for the second facet joint location 114b resulting in two facet joint screws 300*a*, 300*b* being attached to locations 114, 114*b*, respectively (280). Similarly, additional facet screws are driven in other facet joint locations of adjacent vertebras 82 and 86.

Figure 21:
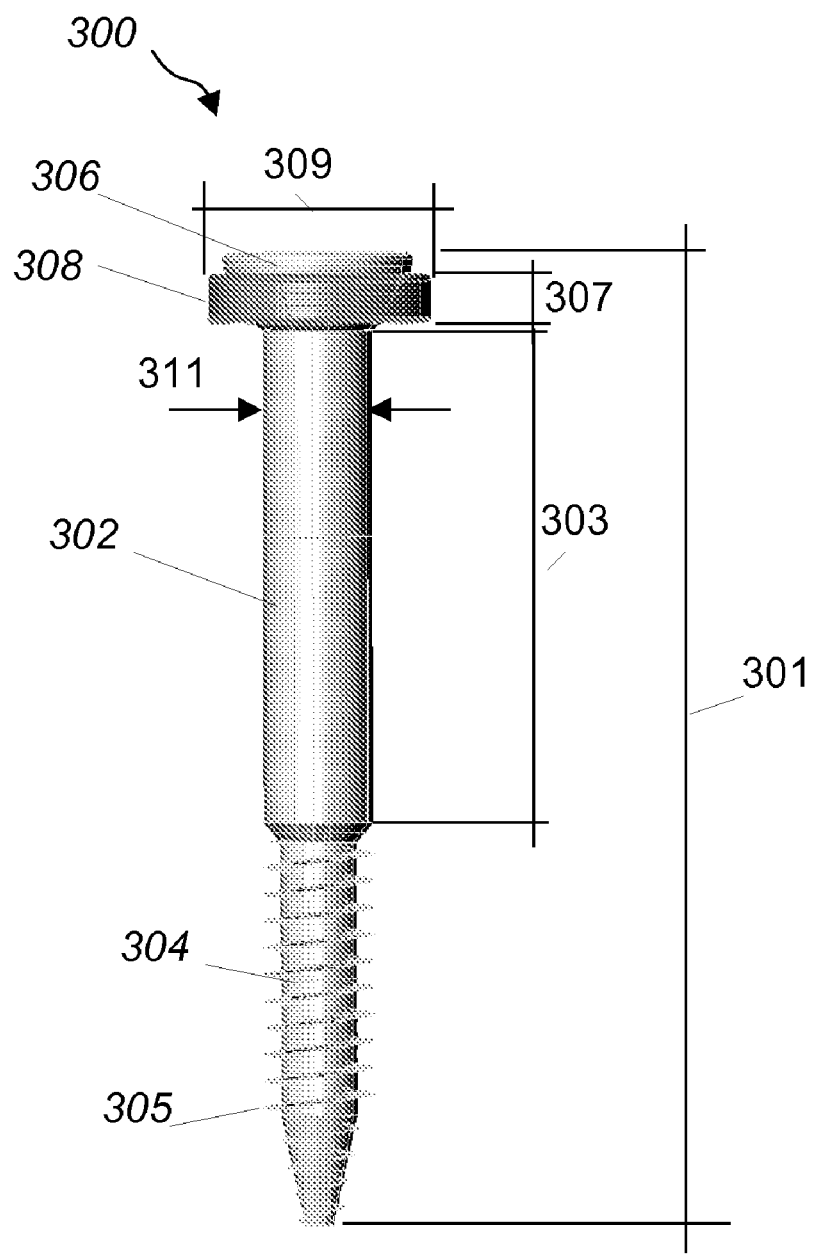
FIG. 21 is a front perspective view of a facet screw.
Figure 22:
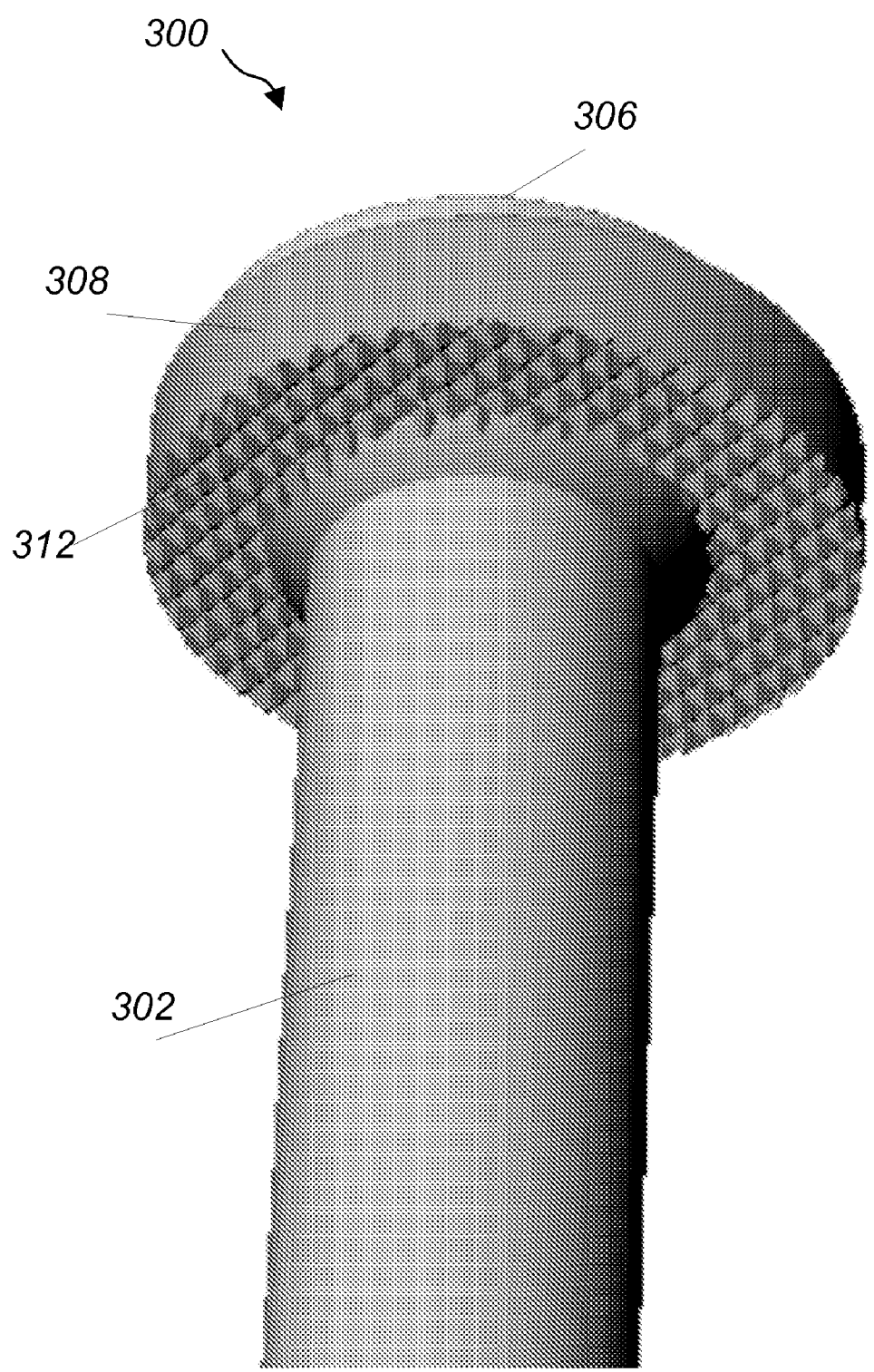
FIG. 22 is a detailed view of the bottom surface of the facet screw ring of FIG. 21.
Figure 23:
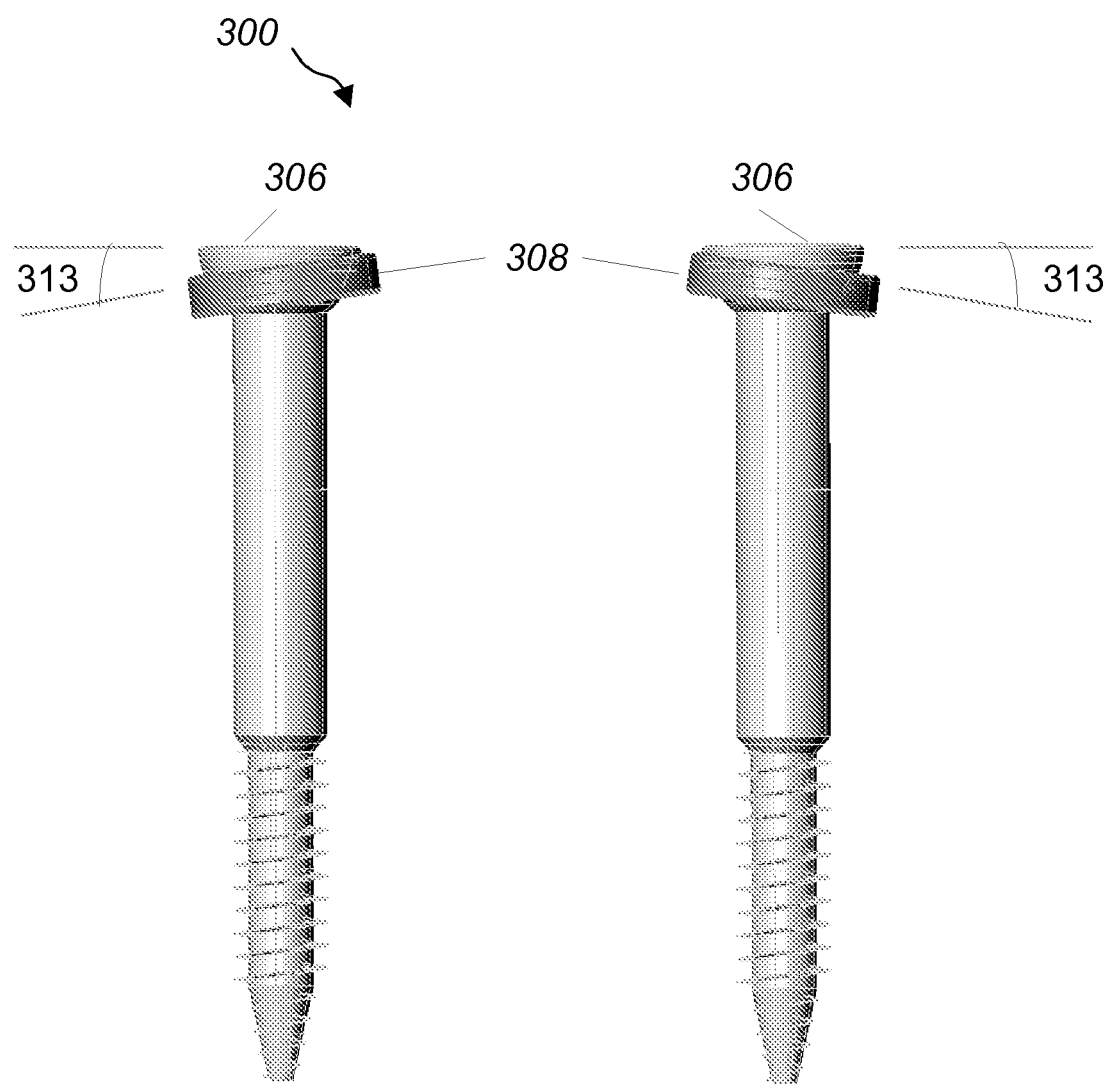
FIG. 23 is a front view of two different orientations of the facet screw ring of FIG. 22.

Referring to FIG. 21, facet screw 300 includes an elongated body 302 having a flat head 306 at one end and a threaded portion 304 at the opposite end. A washer 308 is fitter around head 306. Washer 308 is configured to pivot around the head 306 at an angle 313, as shown in FIG. 23 and has teeth 312 in the bottom surface for holding into the bone, shown in FIG. 22. In one example, facet screw 300 has a length 301 of about 40 millimeters, a non-threaded portion length 303 of 20 millimeters, a width 309 of the head of about 9 millimeters, a body width 311 of 4.5 millimeters, a washer width of 2 millimeters and a washer pivoting angle 313 of 7.5 degrees. Facet screw 300 is manufacture by SpineFrontier, Inc (Beverly, Mass.) and may be made of metal such as stainless steel or titanium, plastic, bioabsorbable material or ceramic.

Other embodiments are within the scope of the following claims. For example, second guide wire may be a non-pivoting K-wire or both first and second guide wires may be pivoting K-wires. The bottom surface of washer 308 may include ridges, serrations, grooves, or spikes.

Several embodiments of the present invention have been described. Nevertheless, it will be understood that various modifications may be made without departing from the spirit and scope of the invention. Accordingly, other embodiments are within the scope of the following claims.

What is claimed is:

1. A system for attaching first and second fixation elements at a predetermined angle relative to each other to first and second locations of a vertebra, respectively, comprising:
   a first guide wire configured to be inserted into said first location of said vertebra;
   an angular guide system comprising first and second guide arms pivotally connected to each other and configured to be set at said predetermined angle relative to each other and wherein said first guide arm is configured to be inserted over said first guide wire;
   a second guide wire configured to be inserted through said second guide arm into said second location of said vertebra, wherein said second guide wire comprises first and second members configured to pivot relative to each other.

2. The system of claim 1 further comprising a dilator configured to be inserted over said guide wires, to dilate tissue around said guide wires and to provide a pathway for inserting and attaching said fixation elements into said locations of said vertebra wherein said dilator comprises an outer dilator cannula and an inner dilator configured to move within said outer dilator cannula and to dilate said tissue.

3. The system of claim 2 further comprising a drill configured to drill into said locations of said vertebra through said outer dilator cannula.

4. The system of claim 3 wherein said drill comprises an adjustable drill depth.

5. The system of claim 4 wherein said drill further comprises an automatic drill stop.

6. The system of claim 2 further comprising a driver configured to insert and attach said fixation elements to said locations through said outer dilator cannula and wherein said driver comprises a fixation element retaining and releasing mechanism.

7. The system of claim 1 wherein said first and second locations comprise one of facet joint, pedicle, transverse processes, pars, lamina, vertebral body, sacrum, lateral mass, or occiput locations.

8. The system of claim 1 wherein said fixation element comprises a screw and said screw comprises an elongated body having a threaded portion at a distal end and a head at a proximal end and a washer configured to be positioned at an angle relative to said head.

9. The system of claim 8 wherein said washer comprises a bottom surface comprising protrusions configured to engage said first location.

10. The system of claim 9 wherein said protrusions comprise one of spikes, teeth, serrations, grooves, or ridges.

* * * * *